(12) United States Patent
Unger

(10) Patent No.: US 10,987,308 B2
(45) Date of Patent: Apr. 27, 2021

(54) THERAPEUTIC NANOPARTICLES AND RELATED COMPOSITIONS, METHODS AND SYSTEMS

(71) Applicant: Genesegues, Inc., Chaska, MN (US)

(72) Inventor: Gretchen M. Unger, Chaska, MN (US)

(73) Assignee: GENESEGUES, INC., Chaska, MN (US)

( * ) Notice: Subject to any disclaimer, the term of this patent is extended or adjusted under 35 U.S.C. 154(b) by 0 days.

(21) Appl. No.: 14/844,828

(22) Filed: Sep. 3, 2015

(65) Prior Publication Data

US 2016/0058706 A1 Mar. 3, 2016

Related U.S. Application Data

(60) Provisional application No. 62/045,519, filed on Sep. 3, 2014.

(51) Int. Cl.
| | | |
|---|---|---|
| *A61K 9/14* | (2006.01) | |
| *A61K 31/7088* | (2006.01) | |
| *A61K 9/51* | (2006.01) | |
| *A61K 9/107* | (2006.01) | |
| *C12N 15/88* | (2006.01) | |

(52) U.S. Cl.
CPC ............ *A61K 9/141* (2013.01); *A61K 9/1075* (2013.01); *A61K 9/5161* (2013.01); *A61K 9/5169* (2013.01); *A61K 31/7088* (2013.01); *C12N 15/88* (2013.01)

(58) Field of Classification Search
CPC .... C01D 17/00; C01D 17/003; C01D 17/006; C01D 15/00; C01D 15/005; C01D 15/02; C01D 15/04; C01D 15/06; C01D 15/08; C01D 15/10

See application file for complete search history.

(56) References Cited

U.S. PATENT DOCUMENTS

| | | |
|---|---|---|
| 4,107,288 A | 8/1978 | Oppenheim et al. |
| 4,177,177 A | 12/1979 | Vanderhoff et al. |
| 4,273,875 A | 6/1981 | Manis |
| 4,304,863 A | 12/1981 | Collins et al. |
| 4,332,901 A | 6/1982 | Goldstein |
| 4,336,336 A | 6/1982 | Silhavy et al. |
| 4,349,629 A | 9/1982 | Carey et al. |
| 4,356,270 A | 10/1982 | Itakura |
| 4,362,867 A | 12/1982 | Paddock |
| 4,363,877 A | 12/1982 | Goodman et al. |
| 4,403,036 A | 9/1983 | Hartley et al. |
| 4,419,450 A | 12/1983 | Dean et al. |
| 4,822,594 A | 4/1989 | Gibby |
| 4,913,908 A | 4/1990 | Couvreur et al. |
| 4,920,016 A | 4/1990 | Allen et al. |
| 4,937,119 A | 6/1990 | Nikles et al. |
| 4,968,350 A | 11/1990 | Bindschaedler et al. |
| 5,013,830 A | 5/1991 | Ohtsuka et al. |
| 5,116,507 A | 5/1992 | Ebbins et al. |
| 5,128,326 A | 7/1992 | Balazs et al. |
| 5,133,908 A | 7/1992 | Stainmesse et al. |
| 5,142,047 A | 8/1992 | Summerton et al. |
| 5,145,684 A | 9/1992 | Liversidge et al. |
| 5,185,444 A | 2/1993 | Summerton et al. |
| 5,188,816 A | 2/1993 | Sherry et al. |
| 5,219,553 A | 6/1993 | Kraft et al. |
| 5,284,646 A | 2/1994 | Menz et al. |
| 5,358,704 A | 10/1994 | Desreux et al. |
| 5,384,133 A | 1/1995 | Boyes et al. |
| 5,387,124 A | 2/1995 | Shinohara et al. |
| 5,439,686 A | 8/1995 | Desai et al. |
| 5,487,390 A | 1/1996 | Cohen et al. |
| 5,492,814 A | 2/1996 | Weissleder |
| 5,498,421 A | 3/1996 | Grinstaff et al. |
| 5,500,224 A | 3/1996 | Vranckx et al. |
| 5,503,851 A | 4/1996 | Mank et al. |
| 5,516,507 A | 5/1996 | N'Guyen et al. |
| 5,554,386 A | 9/1996 | Groman et al. |
| 5,578,709 A | 11/1996 | Woiszwillo |
| 5,580,960 A | 12/1996 | Burgeson et al. |
| 5,589,466 A | 12/1996 | Feigner et al. |
| 5,593,974 A | 1/1997 | Rosenberg et al. |
| 5,610,031 A | 3/1997 | Burgeson et al. |
| 5,625,040 A | 4/1997 | Margolis et al. |
| 5,626,877 A | 5/1997 | Amsden et al. |
| 5,629,021 A | 5/1997 | Wright |
| 5,639,473 A | 6/1997 | Grinstaff et al. |
| 5,639,480 A | 6/1997 | Bodmer et al. |
| 5,646,248 A | 7/1997 | Sawada et al. |

(Continued)

FOREIGN PATENT DOCUMENTS

| | | |
|---|---|---|
| DE | 4341114 | 6/1995 |
| DE | 4411557 | 10/1995 |

(Continued)

OTHER PUBLICATIONS

Ma, X., Effect of alkali metal cations on adsorption of guar gum onto quartz. Thesis, Vancouver : University of British Columbia Library. Published Dec. 10, 2009, pp. 1-82.*
Almarsson et al. (2012) Pharm Pat Analyst 1(3):313-327 "The A to Z of pharmaceutical cocrystals: a decade of fast-moving new science and patents".
Braga et al. (2010) Chem Commun 46:6232-6242 "The growing world of crystal forms".
Brooker (1992) Spectrochimica Acta 48a(7):999-1008 "Raman and Infrared Studies of Lithium and Cesium Carbonates".
Brown et al. (2010) Clin Can Res 16(8):2295-2307 "CK2 Modulation of NF-κB, TP53, and the Malignant Phenotype in Head and Neck Cancer by Anti-CK2 Oligonucleotides in vitro or in vivo via Sub-50-nm Nanocapsules".

(Continued)

*Primary Examiner* — Arthur S Leonard
(74) *Attorney, Agent, or Firm* — Adsero IP

(57) ABSTRACT

Disclosed are targeted sub-50 nanometer nanoparticles suitable for delivering bioactive agents of interest, and related compositions, methods, and systems, which improve the manufacturing, stability, efficacy and other aspects of therapeutic nanoparticles.

67 Claims, No Drawings

Specification includes a Sequence Listing.

(56) References Cited

U.S. PATENT DOCUMENTS

| | | |
|---|---|---|
| 5,648,095 A | 7/1997 | Ilium et al. |
| 5,648,097 A | 7/1997 | Nuwayser |
| 5,648,465 A | 7/1997 | Margolis et al. |
| 5,650,543 A | 7/1997 | Medina |
| 5,679,323 A | 10/1997 | Menz et al. |
| 5,707,606 A | 1/1998 | Quay |
| 5,723,335 A | 3/1998 | Hutcherson et al. |
| 5,736,156 A | 4/1998 | Burke |
| 5,759,582 A | 6/1998 | Leong et al. |
| 5,766,922 A | 6/1998 | Peles |
| 5,770,565 A | 6/1998 | Cheng et al. |
| 5,792,743 A | 8/1998 | Schachner |
| 5,837,313 A | 11/1998 | Ding et al. |
| 5,846,561 A | 12/1998 | Margalit |
| 5,849,865 A | 12/1998 | Cheng et al. |
| 5,858,398 A | 1/1999 | Cho |
| 5,866,165 A | 2/1999 | Liu et al. |
| 5,872,231 A | 2/1999 | Engvall et al. |
| 5,874,111 A | 2/1999 | Maitra et al. |
| 5,891,108 A | 4/1999 | Leone et al. |
| 5,902,795 A | 5/1999 | Toole et al. |
| 5,916,803 A | 6/1999 | Sedlacek et al. |
| 5,922,859 A | 7/1999 | Birnstiel et al. |
| 5,945,100 A | 8/1999 | Fick |
| 5,962,424 A | 10/1999 | Hallahan et al. |
| 5,962,427 A | 10/1999 | Goldstein et al. |
| 5,962,566 A | 10/1999 | Grandfils et al. |
| 5,972,027 A | 10/1999 | Johnson |
| 5,985,832 A | 11/1999 | Roodman et al. |
| 5,990,089 A | 11/1999 | Szoka, Jr. et al. |
| 6,008,192 A | 12/1999 | Al-Razzak et al. |
| 6,033,645 A | 3/2000 | Unger |
| 6,041,252 A | 3/2000 | Walker et al. |
| 6,051,258 A | 4/2000 | Kantor |
| 6,071,305 A | 6/2000 | Brown et al. |
| 6,074,609 A | 6/2000 | Gavin et al. |
| 6,074,659 A | 6/2000 | Kunz et al. |
| 6,074,673 A | 6/2000 | Gullen |
| 6,083,996 A | 7/2000 | Buyuktimkin et al. |
| 6,086,582 A | 7/2000 | Altman et al. |
| 6,086,912 A | 7/2000 | Gilman |
| 6,106,866 A | 8/2000 | Ranney |
| 6,110,498 A | 8/2000 | Rudnic et al. |
| 6,120,536 A | 9/2000 | Ding et al. |
| 6,120,847 A | 9/2000 | Yang et al. |
| 6,121,231 A | 9/2000 | Petit et al. |
| 6,124,260 A | 9/2000 | Sharifi et al. |
| 6,136,295 A | 10/2000 | Edwards et al. |
| 6,139,819 A | 10/2000 | Unger et al. |
| 6,139,870 A | 10/2000 | Verrecchia |
| 6,140,117 A | 10/2000 | Milbrandt et al. |
| 6,142,939 A | 11/2000 | Eppstein et al. |
| 6,143,037 A | 11/2000 | Goldstein et al. |
| 6,143,211 A | 11/2000 | Mathiowitz et al. |
| 6,146,663 A | 11/2000 | Bissery et al. |
| 6,153,729 A | 11/2000 | Stein et al. |
| 6,159,142 A | 12/2000 | Alt |
| 6,159,467 A | 12/2000 | Chung et al. |
| 6,165,440 A | 12/2000 | Esenaliev |
| 6,165,988 A | 12/2000 | Noc et al. |
| 6,174,867 B1 | 1/2001 | Hindsgaul |
| 6,177,103 B1 | 1/2001 | Pace et al. |
| 6,197,346 B1 | 3/2001 | Mathiowitz et al. |
| 6,204,054 B1 | 3/2001 | Sutton et al. |
| 6,232,287 B1 | 5/2001 | Ruoslahti et al. |
| 6,235,313 B1 | 5/2001 | Mathiowitz et al. |
| 6,245,349 B1 | 6/2001 | Yiv et al. |
| 6,251,079 B1 | 6/2001 | Gambale et al. |
| 6,255,457 B1 | 7/2001 | Schnitzer |
| 6,258,121 B1 | 7/2001 | Yang et al. |
| 6,283,947 B1 | 9/2001 | Mirzaee |
| 6,283,949 B1 | 9/2001 | Roorda |
| 6,287,792 B1 | 9/2001 | Pardridge et al. |
| 6,296,832 B1 | 10/2001 | Ruoslahti et al. |
| 6,301,660 B1 | 10/2001 | Benson |
| 6,303,114 B1 | 10/2001 | Metzger et al. |
| 6,303,137 B1 | 10/2001 | Dittgen et al. |
| 6,303,573 B1 | 10/2001 | Ruoslahti et al. |
| 6,306,365 B1 | 10/2001 | Ruoslahti et al. |
| 6,309,375 B1 | 10/2001 | Glines et al. |
| 6,309,380 B1 | 10/2001 | Larson et al. |
| 6,309,410 B1 | 10/2001 | Kuzma et al. |
| 6,317,629 B1 | 11/2001 | Haak et al. |
| 6,319,426 B1 | 11/2001 | Bawendi et al. |
| 6,322,805 B1 | 11/2001 | Kim et al. |
| 6,326,144 B1 | 12/2001 | Bawendi et al. |
| 6,342,250 B1 | 1/2002 | Masters |
| 6,346,272 B1 | 2/2002 | Viegas et al. |
| 6,350,780 B1 | 2/2002 | Garst et al. |
| 6,352,972 B1 | 3/2002 | Nimni et al. |
| 6,353,090 B1 | 3/2002 | Pierschbacher et al. |
| 6,358,556 B1 | 3/2002 | Ding et al. |
| 6,372,714 B1 | 4/2002 | Tanaka et al. |
| 6,379,382 B1 | 4/2002 | Yang |
| 6,383,500 B1 | 5/2002 | Wooley et al. |
| 6,387,124 B1 | 5/2002 | Buscemi et al. |
| 6,387,397 B1 | 5/2002 | Chen et al. |
| 6,395,253 B2 | 5/2002 | Levy et al. |
| 6,404,705 B1 | 6/2002 | Watanabe et al. |
| 6,413,942 B1 | 7/2002 | Feigner et al. |
| 6,416,778 B1 | 7/2002 | Ragavan et al. |
| 6,440,738 B1 | 8/2002 | Wyatt |
| 6,455,307 B1 | 9/2002 | McKay et al. |
| 6,475,995 B1 | 11/2002 | Roy et al. |
| 6,482,410 B1 | 11/2002 | Crossin et al. |
| 6,489,458 B2 | 12/2002 | Hackett et al. |
| 6,506,411 B2 | 1/2003 | Hunter et al. |
| 6,528,481 B1 | 3/2003 | Burg et al. |
| 6,593,308 B2 | 7/2003 | Szoka, Jr. |
| 6,607,916 B2 | 8/2003 | Freier et al. |
| 6,632,671 B2 * | 10/2003 | Unger .................. A61K 9/1075 264/4.1 |
| 6,797,685 B2 | 9/2004 | Zhu et al. |
| 6,835,393 B2 | 12/2004 | Hoffman et al. |
| 7,465,716 B2 | 12/2008 | Szoka, Jr. |
| 7,741,304 B2 | 6/2010 | Slaton et al. |
| 7,927,613 B2 | 4/2011 | Almarsson |
| 9,650,244 B2 | 5/2017 | Unger |
| 2001/0018054 A1 | 5/2001 | Hanna |
| 2001/0019715 A1 | 5/2001 | Hanna |
| 2002/0142045 A1 | 10/2002 | Kararli et al. |
| 2003/0059474 A1 | 3/2003 | Scott et al. |
| 2003/0236214 A1 | 12/2003 | Wolff et al. |
| 2004/0137071 A1 | 7/2004 | Unger |
| 2005/0232895 A1 | 10/2005 | Chen |
| 2006/0018826 A1 | 1/2006 | Unger |
| 2007/0098713 A1 | 5/2007 | Unger et al. |
| 2009/0238883 A1 | 9/2009 | Kren et al. |
| 2010/0173001 A1 | 7/2010 | Unger |
| 2010/0247662 A1 | 9/2010 | Unger |
| 2012/0076735 A1 | 3/2012 | Unger |
| 2014/0155733 A1 | 6/2014 | Peyman |

FOREIGN PATENT DOCUMENTS

| | | |
|---|---|---|
| DE | 19723308 | 12/1998 |
| EP | 0860167 | 8/1998 |
| WO | WO 88/08011 | 10/1988 |
| WO | WO 97/03702 | 2/1997 |
| WO | WO 98/08379 | 3/1998 |
| WO | WO 98/40094 | 9/1998 |
| WO | WO 98/43664 | 10/1998 |
| WO | WO 99/00113 | 1/1999 |
| WO | WO 99/13912 | 3/1999 |
| WO | WO 99/29349 | 6/1999 |
| WO | WO 99/33558 | 7/1999 |
| WO | WO 99/39700 | 8/1999 |
| WO | WO 99/48479 | 9/1999 |
| WO | WO 00/47130 | 8/2000 |
| WO | WO 00/72679 | 12/2000 |
| WO | WO 01/45764 | 6/2001 |
| WO | WO 01/91808 | 6/2001 |
| WO | WO 01/64164 | 9/2001 |
| WO | WO 01/82964 | 11/2001 |

(56) References Cited

FOREIGN PATENT DOCUMENTS

| WO | WO 01/89579 | 11/2001 |
|---|---|---|
| WO | WO 02/09735 | 2/2002 |
| WO | WO 02/100343 | 12/2002 |
| WO | WO 03/087021 | 10/2003 |
| WO | WO 03/087323 | 10/2003 |
| WO | WO 03/087389 | 10/2003 |
| WO | WO 07/130873 | 11/2007 |
| WO | WO 2008/095192 | 8/2008 |
| WO | WO 2009/049089 | 4/2009 |

OTHER PUBLICATIONS

Ding et al. (2013) J Am Chem Soc 135:4450-4456 "Dendrite-Free Lithium Deposition via Self-Healing Electrostatic Shield Mechanism".
Ding et al. (2014) J Phys Chem 118:4043-4049 "Effects of Cesium Cations in Lithium Deposition via Self-Healing Electrostatic Shield Mechanism".
Ma (2009) University of British Columbia Library Thesis 1-82 "Effect of alkali metal cations on adsorption of guar gum onto quartz".
Matsuta et al. (2000) Journal of Electrochemical Society 147(5):1695-1702 "Vibrational Assignments of Lithium Alkyl Carbonate and Lithium Alkoxide in the Infrared Spectra an Ab Initio MO Study".
Ong (2011) Dissertation 193 pages "Crystal Engineering of Molecular and Ionic Cocrystals".
Ong (2011) J Am Chem Soc 133:9224-9227 "2:1 Cocrystals of Homochiral and Achiral Amino Acid Zwitterions with Li + Salts: Water-Stable Zeolitic and Diamondoid Metal -Organic Materials".
Smith et al. (2013) Mal Pharmaceutics 10:4728-2738 "Improving Lithium Therapeutics by Crystal Engineering of Novel Ionic Cocrystals".
Trask (2007) Mol Pharmaceutics 4(13):301-309 "An Overview of Pharmaceutical Cocrystals as Intellectual Property".
Trembley et al. (2014) PLOS One 9(10)e109970:1-12 "Tenfibgen Ligand Nanoencapsulation Delivers Bi-Functional Anti-CK2 RNAi Oligomer to Key Sites for Prostate Cancer Targeting Using Human Xenograft Tumors in Mice".
Unger et al. (2014) Mol Cancer Ther 13(8):2018-2029 "Mechanism and Efficacy of Sub-50-nm Tenfibgen Nanocapsules for Cancer Cell—Directed Delivery of Anti-CK2 RNAi to Primary and Metastatic Squamous Cell Carcinoma".
Abra et al., (1981), Biochem. Biophys. Acta 666:493-503, "Liposome disposition in vivo: dose and vesicle-size effects.".
Acharya et al., (1995), Computerized Medical Imaging and Graphics, 19(1): 325, "Biomedical Imaging Modalities: a tutorial.".
Ahmad et al., (2005), "Targeting CK2 for cancer therapy." Anti-Cancer Drugs, 16(10):1037-1043.
Ahmed K. et al., (2002), Trend Cell Biol 12(5): 226-30, "Joining the cell survival squad: an emerging role for Protein Kinase CK2.".
Akerman et al., (2002), PNAS 99(20):12617-12621,"Nanocrystal imaging in vivo.".
Akhtar et al., (2000), Advanced Drug Delivery Reviews 44:3-21, "The Delivery of Antisense Therapeutics.".
Albert et al., (1998), J. Exp. Med. 188(7):1359-68, "Immature dendritic cells phagocytosis apoptotic cells via avf3.5 and CD36, and cross-present antigens to cytotoxic T lymphocytes.".
Allport et al., (2001), Experimental Hematology 29:1237-1246 "In vivo imaging of gene and cell therapies".
Al-Mousa (1999) J Pharm Pharmacol 51:178, "Evidence for the role of caveolae in gene delivery".
Anderson, (1998), Annu. Rev. Biochem. 67:199-225. "The Caveolae Membrane System.".
Antisense Research and Application (1988) Editor: Stanley T. Crooke, Springer-Verlag, pp. 1-101.
Ash et al., (1993), Handbook of Industrial Surfactants, Gower Publishing Co., pp. 885-905.
Aukhill I. et al., (1993), J Biol. Chem. 268(4):2542-2553, "Cell- and heparin-binding domains of the hexabrachion arm identified by tenascin expression proteins.".

Babiuk, et al. (2000) Journal of Controlled Release, 66:199-214, "Cutaneous vaccination: the skin as an immunologically active tissue and the challenge of antigen delivery".
Bally et al., (1999), Advanced Drug Delivery Reviews 38:291-315, "Biological Barriers to Cellular Delivery of Lipid-Based DNA Carriers.".
Barfoed, et al. (2004) Vaccine 22:1395-1405, "Influence of routes and administration parameters on antibody response of pigs following DNA vaccination".
Barry, B. W., "Dermatological Formulations: Percutaneous Absorption", pp. 127-351. (1983) Marcel Dekker, Inc., New York, NY.
Bello et al., (2001), Cancer Research 61: 8730-36, "Simultaneous inhibition of glioma angiogenesis, cell proliferation, and invasion by a naturally occurring fragment of human metalloproteinase 21.".
Bennet, M. (2003), Heart 89:218-224, "In-stent stenosis: pathology and implications for the development of drug-eluting stents.".
Bijsterbosch, Martin K.; Van De B1LT, Hendrika; and Van Berkel, Theo J.C., "Specific Targeting of a Lipophilic Prodrug of Iododeoxyuridine to Parenchymal Liver Cells Using Lactosylated Reconstituted High Density Lipoprotein Particles," Biochemical Pharmacology, Feb. 1996, vol. 52, pp. 113-121, Copyright 1996 Elsevier Science Inc.
Brand et al., (2000), "Transdermal delivery of antisense compounds." Advanced Drug Delivery Reviews (44) 51-57.
Brannon-Peppas (1997), "Polymers in Controlled Drug Delivery." Medical Plastics and Biomaterials Magazine: 1-17.
Braun et al., (1997), Pharm. Res. 14(10):1472-78,"Protein aggregates seem to play a key role among the parameters influencing the antigenicity of interferon alpha (IFN-α) in normal and transgenic mice.".
Brigger et al., (2002), Adv. Drug Deliv. Rev. 54: 631-651, "Nanoparticles in cancer therapy and diagnosis.".
Bronaugh, et al., (1999), Editors, "Percutaneous Absorption Drugs-Cosmetics-Mechanisms-Methodology", 3rd Ed., pp. 177-193; 597-613, 879-886.
Bruchez, M. Jr., et al., (1998), "Semiconductor nanocrystals as fluorescent biological labels." Science 281(5385):2013-6.
Bulte, J., et al., (2001), "Magnetodendrimers allow endosomal magnetic labeling and in vivo tracking of stem cells." Nat Biotechnol 19(12):1141-7.
Calvo, et al., (1997), "Evaluation of Cationic Polymer-Coated Nanocapsules as Ocular Drug Carriers, International Journal of Pharmaceutics" 153 pp. 41-50.
Calvo, et al., (1995), "Comparative in vitro Evaluation of Several Colloidal Systems, Nanoparticles, Nanocapsules, and Nanoemulsions, as Ocular Drug Carriers", Journal of Pharmaceutical Sciences, pp. 530-536.
Carloni et al., (1996), Gastroent. 110: 1127-36, "Expression and function of integrin receptors for collagen and laminin in cultured human hepatic stellate cells.".
Chapman et al., (1996), Ultramicroscopy 62:191-213, "A characterisation of dark-field imaging of colloidal gold labels in a scanning transmission X-ray microscopy.".
Chen, et al. (2009) Journal of Controlled Release 139:212-220, "Dry-coated microprojection array patches for targeted delivery of immunotherapeutics to the skin".
Choi, et al. (2006) Current Drug Delivery 3:37-45, "Topical DNA vaccination with Dna/Lipid based complex".
Chonn et al., (1998), Adv. Drug Deliv. Reviews 30:73-83, "Recent advances in liposome technologies and their applications for systemic gene delivery.".
Clarke et al., (1998), Journal of Leukocyte Biology 63:163-168,"Myeloid-specific gene expression.".
Companjen, et al. (2001) Archives of Dermatological Research 293:184-190, "A modified ex vivo skin organ culture system for functional studies".
Condon et al., (1996), Nature Med. 2(10): 1122-1127, "DNA-based immunization by in vivo transfection of dendritic cells.".
Cook, P.D. (1998) Antisense Research and Application : Chapter 2: Antisense Medicinal Chemistry, Springer, New York, pp. 51-101.
Cote et al., (1983), Proc. Natl. Acad. Sci. Usa 80:2026-2030, "Generation of human monoclonal antibodies reactive with cellular antigens.".

(56) References Cited

OTHER PUBLICATIONS

Crooke, S.T., Chapter 1: Basic Principles of Antisense Therapeutics pp. 1-50.
Damge et al., (1996), Intestinal Absorption of PLAGA microspheres in the rat , J. Anat., 189 pp. 491-501.
Daniotti et al., "Cloning and Expression of Genes Coding for Protein Kinase CK2 Alpha and Beta Subunits in Zebrafish". Cellular & Molecular Biology Research 1994, vol. 40, (5/6), pp. 431-439 see abstract.
Dean, et al. (2005) Expert Opinion Drug Delivery 2(2):227-236, "Epidermal delivery of protein and DNA vaccines".
Dean, Lange's Handbook of Chemistry, 15th Edition, pp. 1.74-1.343, 10.69-10.73.
Discher and Eisenberg (2002) Science 297:967-973, "Polymer Vesicles".
Do, et al. (2004) Journal of Immunotherapy 27(1):1-12, "Role of CD44 and Hyaluronic Acid (Ha) in Activation of Alloreactive and Antigen-Specific T Cells by Bone Marrow-Derived Dendritic Cells".
Dokka et al., (2000), "Novel non-endocytic delivery of antisense oligonucleotides", Advanced Drug Delivery Reviews (44): 35-49.
Donnelly et al., (2003), Int J Parasitol 33:457-67,"Technical and regulatory hurdles for DNA vaccines.".
Drazba, et al., (1990), "The role of cell adhesion molecules in neurite outgrowth on Mueller cells", Dev. Biol. 138(1):82-93.
Dresser, Mj, "The MDR1 C3425T polymorphism: effects on P-glycoprotein expression/function and clinical significance", AAPS PharmSci, 2001, 3(3): 3, Clinical Pharmacology.
Du, et al (2005) Journal of the American Chemical Society 127:17982-17983, "pH- Sensitive Vesicles Based on a Biocompatible Zwitterionic Diblock Copolymer".
Dubertret et al., (2002), "In Vivo Imaging of Quantum Dots Encapsulated in Phospholipid Micelles", Science 298:1759-1762.
Duquemin et al., "The effect of sodium lauryl sulphate, cetrimide and polysorbate 20 surfactants on complex coacervate volume and droplet size," Journal Pharm Pharmacol, Oct. 1985, 37:698-702, Abstract.
Fattori et al., (2003), "Drug-eluting stents in vascular intervention", The Lancet, 361(1):247-249.
Faust et al., (2000), "Antisense oligonucleotides against Pkcii-a inhibit growth of squamous cell carcinoma of the head and neck in vitro." Head Neck 22:341-346.
Feldman et al., (2000), "Stent-Based Gene Therapy", 10(1&2) J. of Long-Term Effects of Medical Implants, 47-68.
Feng et al., (1996), J Exp. Med 183:1981-1986, "Vesiculo-Vacuolar Organelles and the Regulation of Venule Permeability to Macromolecules by Vascular Permeability Factor, Histamine, and Serotonin.".
Fischer, et al. (2010) Bioconjugate Chemistry 21(6):1018-1022, "Conjugation to nickel-chelating nanolipoprotein particles increases the potency and efficacy of subunit vaccines to prevent West Nile encephalitis".
Flaherty et al., (1995), "Phenotypic modulation of aortic smooth muscle cells using optimized cell culture environments." Mol Cell Biol. 65:27a. Tech Bulletin #425, http:// www. bdbio.com.
Foged et al., (2002), "Targeting vaccines to dendritic cells", Pharm Res. 19(3):229-238.
Foldvari, et al. (2010) Molecular Pharmaceutics 7(3):751-762, "Topical evidence of interferon alpha by biphasic vesicles: Evidence for a novel nanopathway across the stratum corneum".
Frechet, J., "Functional polymers and dendrimers: reactivity, molecular architecture, and interfacial energy." Science 263(5154):1710-5, 1994.
Froehler et al., (1988), "Phophoramidate analogues of DNA: synthesis and thermal stabililty of heteroduplexes." Nucleic Acids Res. 156:4831-4839.
Gapany et al., (1995), "Association of elevated protein kinase CK2 activity with aggressive behavior of squamous cell carcinoma of the head and neck." 1(6): 65966.

Gaur et al., (2000), "Biodistribution of fluoresceinated dextran using novel nanoparticles evading reticuloendothelial system", International Journal of Pharmaceutics:1-10.
Gautschi et al., (2001) J. Of National Cancer Institute 93(6):463-471 "Activity of a Novel bcl-2/bcl-xL-Bispecific Antisense Oligonucleotide Against Tumors of Diverse Histologic Origins".
Gerdts, et al. (2007) Future Microbiology 2(6):667-675, "Use of animal models in the development of human vaccines".
Gennaro, "Remington: the Science and Practice of Pharmacy", 20th Ed., Lippincott Williams & Wilkins, pp. 288-334; 721-752; 836-857 and 903-929.
Gerner et al., (1998), "Similarity Between Nuclear Matrix Proteins of Various Cells Revealed by an Improved Isolation Method." Journal of Cellular Biochemistry (71) 363-374.
Ghosh, et al., 1997, "Transdermal and Topical Drug Delivery Systems" Interpharm Press, Inc., Buffalo Grove, Illinois. (pp. 46-49 and 156-157 and 200-201).
Glinsky et al., (2001), "The role of Thomsen-Friedenreich antigen in adhesion of human breast and prostate cancer cells to the endothelium." Cancer Research 61:4851-57.
Golan et al., (1999), "DNA Toroids: Stages in Condensation." Biochemistry (38): 14069-14076.
Gopferich (1995), "Polymer Degradation and Erosion: Mechanisms and Applications." Eur. J. Pharm. Biophar. 42(1):1-11.
Grauer et al., (2002), "Analysis of maturation states of rat bone marrow-derived dendritic cells using an improved culture technique.", Histochem Cell Biol. 117:351-362.
Grayson et al., (2001), "Convergent dendrons and dendrimers: from synthesis to applications." Chem Rev 101(12): 3819-68.
Guermonprez et al., (2002), Ann. Rev. Immunol. 20:621-67, "Antigen presentation and T cell stimulation by dendritic cells.".
Gumbleton, Mark; Abulrob, Abedel-nasser G; and Campbell, Lee, "Caveolae: an Alternative Membrane Transport Compartment," Pharmaceutical Research, vol. 17, No. 9, May 2000, pp. 1035-1048, Plenum Publishing Corporation.
Halin et al., (2002), "Enhancement of the antitumor activity of interleukin-12 by targeted delivery to neovasculature", Nature Biotech., vol. 20, pp. 264269.
Hasan et al., (1999), J Immunol Methods 229:1-22,"Nucleic acid immunization: concepts and techniques associated with third generation vaccines.".
Harada et al., (2001), European Journal of Pharmaceutical Sciences 13:3542, "Physiochemical Properties and Nuclease Resistance of Antisense-Oligodeoxynucleotides Entrapped in the Core of Polyion Complex Micelles Composed of Poly(ethylene Glycol)-Poly(L-Lysine) Block Copolymers.".
Heath, J. (1998), Nature 393: 730-1,"Fullerenes: C60's smallest cousin.".
Hein, et al. (2002) Nature Reviews Immunology 3:79-85, "A road less travelled: large animal models in immunological research".
Hengge (2006) Gene Therapy 13:1555-1563, "Gene therapy progress and prospects: the skin easily accessible, but still far away".
Hermanson, (1996), Bioconjugate Techniques, Academic Press, San Diego, 15 pages.
Hirao (2008) Vaccine 26:440-448, "Intradermal/subcutaneous immunization by electroporation improves plasmid vaccine delivery and potency in pigs and rhesus macaques".
Hornberger et al., (2000), Circ Res. 87(6):508-15, "Synthesis of extracellular matrix and adhesion through 131 integrins are critical for fetal ventricular myocyte proliferation.".
Huang (2007) Semin Immunopathol 29:71-80, "Topical vaccination: the skin as a unique portal to adaptive immune responses".
Hunt et al., (1992), J. Biomed. Mat. Res. 26: 819-828, "Stimulation of neutrophil movement by metal ions.".
Hussain (2004) J. of Controlled Release 99:139-155 "A novel anionic dendrimer for improved cellular delivery of antisense oligonucleotides".
Hussain, N., (2000), Adv. Drug Deliv. Rev. 43:95-100,"Ligand-mediated tissue specific drug delivery.".
Inaba et al., (1995), Cell Immunol. 163:148-156, "Tissue distribution of the DEC-205 protein that is detected by the monoclonal antibody NLDC-145.".

(56) References Cited

OTHER PUBLICATIONS

Inactive Ingredient Guide (1996), Division of Drug Information Resources, FFDA, 22 pages.
International Search Report (PCT/US03/10850) from corresponding PCT application dated Dec. 11, 2003 (7 pages).
International Search Report (PCT/US03/10854) from corresponding PCT application dated Dec. 5, 2003 (3 pages).
Ishii, et al. (2001) Journal of Investigative Dermatology Symposium Proceedings 6(1):76-80, "Immunologic Characterization of HIV-specific DNA vaccine".
Iwasaki, et al. (2010) Science 327:291-295, "Regulation of adaptive immunity by the innate immune system".
Jacob et al., Cancer Research (1999), 59:4453-57, "Osteonectin promotes prostate cancer cell migration and invasion: a possible mechanism for metastasis to bone.".
Jain, Sci. American (1994,) 7:58-65, "Barriers to drug delivery in solid tumors.".
Janes, et al., (2001), "Polysaccharide Colloidal Particles as Delivery Systems for Macromolecules," Advanced Drug Delivery Reviews, 47 pp. 83-97.
Janeway et al., (2002), Ann. Rev. Immunology 20:197-216,"Innate immune recognition.".
Johansen et al., (2000), Eur J. Pharm. Biopharm. 50:129-146, "Revisiting Pla/Plga microspheres: an analysis of their potential in parenteral vaccination.".
Johnstone, R., Nature Rev. Drug Disc. (2002), 1:287-299,"Histone-deacetylase inhibitors: novel drugs for the treatment of cancer.".
Kamath et al., Infect Immun, (1999), 67: 1702-1707, "Differential Protective Efficacy of DNA Vaccines Expressing Secreted Proteins of Mycobacterium tuberculosis".
Katoaka, et al., (2001), "Block Copolymer Micelles for Drug Delivery: Design, Characterization and Biological Significance." Advanced Drug Delivery Reviews, 47 pp. 113-131.
Kawashima, (2001), "Nanoparticle Systems for Improved Drug Delivery." Advanced Drug Delivery Reviews, 47 pp. 1-2.
Kibbe, Arthur H. Editor, (1986), Handbook of Pharmaceutical Excipients, American Pharmaceutical Association 2000, Third Edition, pp. 94-95, 117-120.
Klinman et al., (1998), J Immunol 160: 2388-2392,"Contribution of cells at the site of DNA vaccination to the generation of antigen-specific immunity and memory.".
Kohler et al., (1975), Nature 256:495-497, "Continuous cultures of fused cells secreting antibodies of predefined specificity.".
Kondo, et al., "Rapid isolation of plasmid DNA by Lia-ethidium bromide treatment and gel filtration," Anal Biochem, (1991), 198(1): 30-35, Abstract.
Koltover (2000) PNAS 97(26):14046-14051 DNA condensation in two dimensions.
Koukoulis, et al., (1991), "Tenascin in normal, reactive, hyperplastic and neoplastic tissues: biologic and pathologic implications." Hu Pathol. 22: 636643.
Kozbor et al., (1983), Immunology Today 4:72-79, "The production of monoclonal antibodies from human lymphocytes.".
Kratohvil (1986) Advances in Colloid and Interface Science 26:131-154, "Size of Bile Salt Micelles: Techniques, Problems and Results".
Kreuter, (1996), "Mini-review: Nanoparticles and Microparticles for Drug and Vaccine Delivery", J. Anat., 189: 503-505.
Kreuter, (2001), "Nanoparticulate Systems for Brain Delivery of Drugs," Advanced Drug delivery Reviews, 47 pp. 65-81.
Kreuter, (1991), Chapter 6: Nanopaticles-Preparation and Applications, Microcapsules and Nanoparticles in Medicine and Pharmacy, pp. 125-148.
Kreuter (1991), Journal of Controlled Release, 169-176, "Nanoparticle-Based Drug Delivery Systems.".
Krieg et al., (2002), Ann Rev. Immunol. 20:700-60, "CpG motifs in bacterial Dna and their immune effects".
Kronenwett et al., (2000), Stem Cells 18(5)320-330, "The role of cytokines and adhesion molecules for mobilization of peripheral stem cells.".

Lackey et al., (2002), Bioconjugate Chem. 13, 996-1001," a biomimetic pH-responsive polymer directs endosomal release and intracellular delivery of an endocytosed antibody complex.".
Lafleur et al., (1997), J. Biol. Chem. 272(52):32798-32803,"Aortic smooth muscle cells interact with tenascin-C through its fibrinogin-like domain.".
Lakkaraju et al., (2001), J. Biol. Chem. 276(34):32000-007, "Neurons are protected from excitotoxic death by p53 antisense oligonucleotides delivered in anionic liposomes.".
Lamaze, et al., (1995), "The Emergence of Clathrin-Independnet Pinocytic Pathways, "Current Opinion in Cell Biology, 7 pp. 573-580.
Larregina et al., (1997), Immunol. 91:303-13,"Pattern of cytokine receptors expressed by human dendritic cells migrated from dermal explants.".
Lebedeva (2000) European J. Of Pharmaceutics and Biopharmaceutics 50:101-119 "Cellular delivery of antisense oligonucleotides".
Lee et al., (1997), Crit. Rev. Ther. Drug Car. Sys., 14:2 173-206, "Lipidic vector systems for gene transfer.".
Lesley, et al. (2000) Journal of Biological Chemistry 275(35):26967-26975, "Hyaluronan binding by cell surface CD44".
Lewin et al., (2000), Nat. Biotechnol., 18(4):410-4, "Tat peptide-derivatized magnetic nanoparticles allow in vivo tracking and recovery of progenitor cells.".
Li et al., (2000), "Nonviral gene therapy: promises and challenges." Gene Therapy (7): 31-34.
Lieberman, et al., (1996), Pharmaceutical Dosage Forms: Disperse Systems, vol. 2, Second Edition, pp. 1-109.
Lide, Editor in Chief, Crc Handbook of Chemistry and Physics: a Ready-Reference Book of Chemical and Physical Data, Chemical Rubber Publishing Co, 81st, (2000), pp. 7-7 to 7-9; 16-10 to 16-11; 16-43 to 16-47; Appendix.
Lipscomb et al., (2001), Physiol. Rev. 82:97-130, "Dendritic cells: immune regulators in health and disease.".
Lisziewicz, et al. (2004) Journal of Investigative Dermatology 124(1):160-169, "Dermavir A novel topical vaccine for HIV/AIDS".
Liu M. A., (2003), J Int Med 253:402-410,"DNA vaccines: a review.".
Livant et al., (2000), Can Rsrch, 60:309-320, "Anti-invasive, antitumorigenic, and Anitmetastiatic Activities of the PHSCN Sequence in Prostate Carcinoma".
Mahe, et al. (2009) Journal of Investigative Dermatology 129:1156-1164, "Nanoparticle-based targeting of vaccine compounds to skin antigen-presenting cells by hair follicles and their transport in mice".
Manome et al., (1999), Immunol. 98:481-490, "Simple chemicals can induce maturation and apoptosis of dendritic cells.".
Maragou et al., (1999), Oral Disease, 5:20-6, "Alteration of integrin expression in oral squamous cell carcinomas.".
Martin et al., (1997), Development 124(19): 3909-3917, "Integrins mediate adhesion to agrin and modulate agrin signaling.".
Martin et al., (2000), Int. J. Rad. Oncol. Biophys. 47(2): 277-90,"TGF-ß1 and radiation fibrosis: a master switch and a specific therapeutic target?".
Mastrobattista E., Van Der Aa, M.A.E.M., Hennink, W.E., and Crommelin, D.J.A., Artificial Viruses: A Nanotechnological Approach to Gene Delivery, Nature Reviews Drug Discovery, 2006, vol. 5, pp. 115-120, Nature Publishing Group.
Matveev et al., (2001), Adv Drug Deliv Rev 49:237-250,"The role of caveolae and caveolin in vesicle-dependent and vesicle-independent trafficking.".
Merdan et al., (2002), Adv Drug Deliv Rev 54:715-758, "Prospects for cationic polymers in gene and oligonucleotide therapy against cancer.".
Micic et al., (1997), "Size-dependent spectroscopy of InP quantum dots." J. Phys Chem. B., 101(25):4904-12.
Miller et al., (1979), Biochem. 18:5134-5143, "Nonionic nucleic acid analogs Synthesis and characterization of dideoxyribonucleoside methylphophonates.".
Miller et al., (1980), J. Biol. Chem. 255:9659-9665, "Oligothymidylate analogues having stereoregular, alternating methylphosphonate/phosphodiester backbones.".

(56) References Cited

OTHER PUBLICATIONS

Mizrahy, et al. (2011) Journal of Controlled Release 156:231-238, "Hyaluronan-coated nanoparticles: The influence of the molecular weight on CD44-hyaluronan interactions and on the immune response".
Modlin, (2000), "A toll for DNA vaccines." Nature (408): 659-660.
Mohacsi et al., (1997), J Heart Lung Transplant 16:484-92," Different inhibitory effects of immunosuppressive drugs on human and rat aortic smooth muscle and endothelial proliferation stimulated by PDGF or ECGF.".
Moingeon, (2002), J. Biotech. 98:189-98, "Strategies for designing vaccines eliciting Thl responses in humans.".
Moroi (1941) Plenum Press, Chapter 4, pp. 44-47, Micelles, Theoretical and Applied Aspects.
Muller et al., (2001), "Nanosuspensions as Particulate Drug Formulations in Therapy Rationale for Development and What We Can Expect for the Future," Advanced Drug Delivery Reviews, 47 pp. 3-19.
Nabi Et. Al., (2003), J Cell Biology 161(4):673-77, "Caveolae/raft-dependent endocytosis.".
Nagano et al., "Extracellular matrix modulates the proliferation of rat astrocytes in serum-free culture," Glia., vol. 8, p. 71-6.
Nie, et al., (1997), "Probing single molecules and single nanoparticles by surface-enhanced raman scattering." Science 275(5303):1102-6.
Nielsen et al., (1991), Science 254:1497-1500, "Sequence-selective recognition of DNA by strand displacement with a thymine-substituted polyamide.".
Nishioka et al., (2001), "Lymphatic Targeting with Nanoparticulate System," Advanced Drug Delivery Reviews, 47 pp. 55-64.
Noonberg, et al., (1993), Characteristics of Oligonucleotide Uptake in Human Keratinocyte Cultures. The Journal of Investigative Dermatology (101): 727-731.
Norde (1997) Polymeric Dispersions: Principles and Applications pp. 541-555 Kluwer Academic Publishers, Netherlands "Interaction of Proteins with Polymeric and Other Colloids".
Norman et al., (2000), Gene Ther. 7:1425-1430, "Liposome-mediated, nonviral gene transfer induces a systemic inflammatory response which can exacerbate pre-existing inflamation.".
Nystrom, Robert F., and Brown, Weldon G., "Reduction of Organic Compounds by Lithium Aluminum Hydride. II. Carboxylic Acids," University of Chicago, Geo. Herbert Jones Lab, Oct. 1947, pp. 2548-2549.
O'Hagan et al., (2001), J Virol 75(19):9037-43,"Induction of potent immune responses by cationic microparticles with adsorbed human immunodeficiency virus DNA vaccines.".
Otten et al., (2000), Intervirology 43:227-232,"Relative potency of cellular and humoral immune responses induced in DNA vaccination.".
Ouchi, T., "Architecture of Polymer Micelles from Block-Copolymers of Lactide and Depsipeptide as Drug Carriers", Polymer Preprints, 41(2) 1637-38 (2000).
Parton, Robert G. And Lindsay, Margaret, "Exploitation of Major Histocompatibility Complex Class I Molecules and Caveolae by Simian Virus 40," Immunological Reviews, vol. 168, 1999, pp. 23-31.
Pelkmans et al., (2001), Nature Cell Biology (3): 473-83 "Caveolar endocytosis of simian virus 40 reveals a new two-step vesicular-transport pathway to the ER.".
Perry'S Chemical Engineers' Handbook, (1934), 7th Ed. pp. 2-24 to 2-47.
Pham et al., (2000), Am. J. Phys. Heart Circ Physiol 279(6): H2916-26, "Striated muscle-specificßld-integrin and FAK are involved in cardiac myocyte hypertrophic response pathways.".
Pilling, et al. (2002) Toxicologic Pathology 30(3):298-305, "The assessment of local tolerance, acute toxicity, and DNA biodistribution following particle-mediate delivery of a DNA vaccine to minipigs".
Pinto, et al., (1999), Pellets as carriers of solid lipid nanoparticles (SLN) for oral administration of Drugs, Pharmazie, 54 pp. 506-509.
Pitha et al., (1970), Biochim. Biophys. Acta 204:39-48, "Polyvinyluracil: the preparation and interactions with adenosine derivatives.".

Pitha et al., (1970), Biopolymers 9:965-977, "Preparation and properties of poly-9-vinyladenine.".
Powell and Horton (2005) Immunologic Research 32(1):207-218, "Threat matrix Low-molecular-weight hyaluronan (HA) as a danger signal".
Quintanar-Guerrero et al., (1998), "Preparation Techniques and Mechanisms of Formation of Biodegradable Nanoparticles from Performed Polymers." Drug Development and Industrial Pharmacy, 24(12): 1113-1128.
Quintanar-Guerrero (1996) International J. of Pharmaceutics 143:133-141 "Influence of stabilizing agents and preparative variables on the formation of poly(D,L-lactic acid) nanoparticles by an emulsification-diffusion technique".
Reiss et al., (1997), Breast Cancer Research & Treatment 45(1):81-95, "Transforming growth factor-beta in breast cancer, a working hypothesis.".
Richardson (2002) Stem Cells 20:105-118 "Gene repair and transposon-mediated gene therapy".
Rolland, (1998), "From Genes to Gene Medicines: Recent Advances in Nonviral Gene Delivery." Critical Reviews in Therapeutic Drug Carrier Systems 15(2):143198.
Roth M., and Hemplelmann, R., "Nanocrystalline LiF via Microemulsion Systems," Journal of Materials Chemistry, 1999, vol. 9, pp. 493-497, RSC Publishing.
Rouselle et al., (2000), Molecular Pharmacology, 57:679-686, "New advances in the transport of doxorubicin through the blood-brain barrier by a peptide vector-mediated strategy.".
Rudginsky et al., (2001), Gene Ther. 4(4):347-355), "Antitumor activity of cationic lipid complexed with immunostimulatory DNA".
Sakuma et al., (2001), "Design of Nanoparticles Composed of Graft Copoly-mers for Oral Peptide Delivery," Advanced Drug Delivery Reviews, pp. 21-37.
Sasaki et al., (2001), Nature Biotech 19: 543-47, "Apoptosis-mediated enhancement of DNA-raised immune responses by mutant caspases.".
Sazani et al., (2002), Nature Biotechnology, 20:1228-33, "Systemically delivered antisense oligomers upregulate gene expression in mouse tissue.".
Scheule, (2000), Adv Drug Delivery Rev 44:119-134,"The role of CpG motifs in immunostimulation and gene therapy.".
Scheibner, et al. (2006) Journal of Immunology 177:1272-1281, "Hyaluronan Fragments Act as an Endogenous Danger Signal by Engaging TLR2".
Schmidt, et al., (1997), "Incorporation of Polymeric Nanoparticles into Solid Dosage Forms," Journal of Controlled Release, 57 pp. 115-125.
Schneider et al., (1998), FEBS Letters 429:269-273, "A novel peptide, Plaeidgielty, for the targeting of alpha9betal-integrins.".
Schramm (1993) American Chemical Society, pp. 14, 105, 168, "The Language of Colloid and Interface Science, a Dictionary of Terms".
Schreder et al., (2000), "CdTe/CdS clusters with "core shell" structure in colloids and films: The path of formation and thermal breakup." J. Phys. Chem. B.,104(8):1677-85.
Senger et al., "Osteopontin at the tumor/host interface. Functional regulation by thrombin-cleavage and consequences for cell adhesion," Ann NY Acad Sci., vol. 760, pp. 83-100.
Shoji (2004) Current Pharmaceutical Design 10(7):785-796 "Current Status of Delivery Systems to Improve Target Efficacy of Oligonucleotides".
Sigma Company Catalog, Sigma Biochemical and Reagents for Life Science Research, St. Louis, MO. p. 1918.
Simpson et al., (2002), Amer. J. of Path. 161(3): 849-857, "Inhibition of Prostate Tumor Cell Hyaluronan Synthesis Impairs Subcutaneous Growth and Vascularization in Immunocompromised Mice".
Simpson et al., (2001), J Biol. Chem 276(21): 17949-57, "Hyaluronan synthase elevation in metastatic prostate carcinoma cells correlates with hyaluronan surface retention, a prerequisite for rapid adhesion to bone marrow endothelial cells.".
Singh et al., (2002), Pharm Res. 19(6):715-28, "Recent advances in vaccine adjuvants.".

(56) References Cited

OTHER PUBLICATIONS

Slaton JW, Unger GM, Sloper DT, Davis AT, Ahmed K., "Induction of apoptosis by antisense CK2 in human prostate cancer xenograft model," Mol Cancer Res., Dec. 2004, 2 (12): 712-721,.
Smith et al. (1995), Percutaneous Penetration Enhancers, pp. 5-20.
Sponsel et al., (1996), Am J. Phys (Cell Physiol.. 40) 271:c721-c272, "Mechanisms of recovery from mechanical injury of cultured rat hepatocytes.".
Stoitzner et al., (2001), J Invest Dermatol 118:117-125,"A closeup view of migrating langerhans cells in the skin.".
Storm et al., (1998), Clin. Can. Res. 4: 111-15, "Doxorubicin entrapped in sterically stabilized liposomes: effects on bacterial blood clearance capacity of the mononuclear phagocyte system.".
Summerton and Weller, (1997), Antisense Nuc. Acid Drug Devel. 7:187195, "Morpholino Antisense Oligomers: Design, Preparation, and Properties.".
Swindle (2008) Technical Bulletin, Sinclair Research, pp. 1-4, "Porcine integumentary system models: Part 1—Dermal toxicology".
Takeuchi et al., (2001), "Mucoadhesive Nanoparticle Systems for Peptide Drug Delivery," Advanced Drug Delivery Reviews, pp. 39-54.
Tawfic et al., (2001), Histol Histopathol 16:573-82, Protein kinase CK2 signal in neoplasia.
Termeer et al. (2001) Journal of Leukocyte Biology 70:715-722, "The role of CD44 during CD40 ligand-induced dendritic cell clustering and migration".
Thompson, Jr., Guy a, and Lee, Pearl, "Studies of the a-Glyceryl Ether Lipids Occurring in Mulluscan Tissues," Biochimica et Biophysica Acta, vol. 98, 1965, pp. 151159.
Timares et al., (2003), J Immunol 170:5483-5490 "Drug-inducible, dendritic cell-based genetic immunization.".
Torchilin, Vladimir P. Ph.D., Edited Handbook of Targeted Delivery, CRC Press, pp. 3-101, 103-117, 119-147, 149-173, 177-192, 218-227, 259-288, 365-384, 429-443, 487-500, 523-552 and 597-609, 1995.
Tousignant et al., (2000), Hu. Gene Ther. 11: 2493-2513, "Comprehensive analysis of the acute toxicities induced by systemic administration of cationic lipid: plasmid DNA complexes in mice.".
Tsai et al., (2002), J. Biol. Chem 277(35):31826-33, "Regulation of histone deacetylase by protein CK2.".
Tsujii, Kaoru (1998) Academic Press, pp. 95-96, Surface Activity: Principles, Phenomena and Applications.
Tuxhorn et al., J Urol. (2001), 166:2472- 2483, "Reactive stroma in prostate cancer progression.".
Unger et al., (2003), AACR Proceedings, 44: 1473, "Antisense formulation via sub50-nm nanoencapsulation enhances effectiveness of problematic medicinal chemistry for tumor-specific antisense to PK CK2.".
Unger et al., (2002), Proceedings of the American Association for Cancer Research 43:577, "Effective chemotherapeutic activity by sub50-nm nanocapsule antisense to protein kinase CK2 for eradication of in vitro tumor nests via targeted caeolar-mediated endocytosis".
Unger et al., (2001), Aaps Pharmsci 3(3) Supplement: 3731, "Effective penetration of in vitro tumor nests by very small nanocapsules for DNA delivery".
Unger (2004) Sbir Website Abstract [Online] p. 1, "s50 nanocapsules for transcutaneous DNA vaccination"; Available Web Site: http://www.sbir.gov/sbirsearch/detail/173406 Last update: unknown; Accessed on: Sep. 10, 2011.
United States Pharmacopeia, 1981 United States Pharmacopeia Dispensing Information, 2 pages.
Varga et al., (2000), Biotechnology and Bioengineering 70(6):593-605, "Receptor-mediated Targeting of Gene Delivery Vectors: Insights from Molecular Mechanisms for Improved Vehicle Design.".
Varner et al., (1995), Cell Ad Commun 3:367-374, "The integrin $av\beta 33$: angiogenesis and apoptosis.".
Vigushin et al., (2002), Anti-cancer drugs, 13:1-13, "Histone deacetylase inhibitors in cancer treatment.".
Vile, et al., "Millennium Review, Cancer Gene Therapy: Hard Lessons and New Courses," Gene Therapy (2000) 7, pp. 2-8.
Virmani et al., (2002), Circulation 106: 2649-2651," Mechanism of late in-stent restenosis after implantation of a paclitaxel derivate-eluting polymer stent system in humans.".
Vogt, et al. (2006) Journal of Investigative Dermatology 126:1316-1322, "40 nm, but not 750 or 1,500 nm, nanoparticles enter epidermal CD1a +cells after transcutaneous application on skin".
Wang et al., (2006), "CK2 Signaling in Androgen-Dependent and Independent Prostate Cancer," J. Cell Biochem, 99(2):382-391.
Wang et al., (1995), Am. J Surg. 170(5) 502-5, "The effect of thrombospondin on oral squamous carcinoma invasion of collagen.".
Wang, G., Ahmad K.A., Unger G., Slaton J.W., Ahmed K., "Downregulation of CK2 induces apoptosis in cancer cells—a potential approach to cancer therapy," Mol Cell Biochem, Jun. 2005, 274 (1-2): 77-84.
Weeratna et al., (2000), Intervirology 43:2128-226, "Optimization strategies for DNA vaccines.".
Werling et al., (1999), J Leuko Biol 66:50-68,"Involvment of caveolae in the uptake of respiratory syncytial virus antigen by dendritic cells.".
Wolfert (1996) Gene Therapy 3:269-273 "Atomic force microscopic analysis of the influence of the molecular weight of poly(L)lysine on the size of polyelectrolyte complexes formed with DNA".
Wolff et al., (1992), J Cell Sci 103:1249-59, "Expression of naked plasmids by cultured myotubes and entry of plasmids into T tubules and caveolae of mammalian skeletal muscle.".
Wong, (Jun. 18, 1991), "Chemistry of Protein Conjugation and Cross-Linking" CRC Press; Table of Contents.
Wood, Randall and Snyder, Fred, "Quantitative Determination of Alk-l-enyl- and Alkyl-Glyceryl Ethers in Neutral Lipids and Phospholipids," Lipids, vol. 3, No. 2, 1967, pp. 129-135.
Wu et al., "Receptor-mediated Gene Delivery and Expression in Vivo." J. Biol. Chem. Oct. 15, 1988. vol. 263, No. 29, pp. 14621-14624, entire documents.
Wu, Yunqiu; Unger, Evan C., Mccreery, Thomas P.; Sweitzer, Robert H.; Shen, Dekang;, Wu, Guanli; and Vielhauer, Matthew D., "Binding and Lysing of Blood Clots Using MRX-408," Investigative Radiology Journal, vol. 33(12), Dec. 1998, pp. 880-885, Copyright 1998 Lippincott Williams & Wilkins, Inc.
Yamamoto et al., (1999), J. Biol. Chem., (274) 31: 21840-21846, "Induction of Tenascin-C in Cardiac Myocytes by Mechanical Deformation".
Yan et al., (1998), J. Histochem Chem 46(1):3-10, "Sparc is expressed by ganglion cells and astrocytes in bovine retina.".
Yan, et al. (2009) HIV/AIDS—Research and Palliative Care 1:1-11, "Lipid nanoparticles with accessible nickel as a vaccine delivery system for single and multiple HIS-tagged HIV antigens".
Yu et al., "The specific delivery of proteins to human liver cells by engineered Bio-nanocapsules." FEBS Journal. 2005, vol. 272, pp. 3651-3660, entire document.
Yuan et al., (1994), "Microvascular Permeability and Interstitial Penetration of Sterically Stabilized (stealth) Liposomes in a Human Tumor Xenograft." Cancer Research (54) 3352-3356.
Zhang et al., (1997), "Comparison of Integrins in Human Skin, Pig Skin, and Perfused Skin: An in Vitro Skin Toxicology Model." Journal of Applied Toxicology 17(4): 247-253.

\* cited by examiner

THERAPEUTIC NANOPARTICLES AND RELATED COMPOSITIONS, METHODS AND SYSTEMS

STATEMENT REGARDING GOVERNMENT RIGHTS

This invention was made with government support under Contract No. HHSN261201300030C awarded by the National Institutes of Health. Thus, the government has certain rights in the invention.

RELATED APPLICATIONS AND INCORPORATIONS BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

SEQUENCE LISTING

The instant application contains a Sequence Listing, which has been submitted electronically in ASCII format and is hereby incorporated by reference in its entirety. Said ASCII copy, created on Sep. 1, 2015, is named 0269.13US_SL.txt and is 9,515 bytes in size.

BACKGROUND

Effective delivery of agents of interest to cells, tissues, organs, and organisms has been a challenge in biomedicine, imaging, and other fields where delivery of molecules of various sizes and dimensions to a predetermined target is desirable. Whether for pathological examination, therapeutic treatment, or fundamental biology studies, several methods are known and used for delivering various classes of biomaterials and biomolecules, which are typically associated with a biological and/or chemical activity of interest. As the number of molecules suitable to be used as chemical or biological agents (e.g., drugs, biologics, therapeutic or imaging agents) increases, development of a delivery system suitable for use with compounds of varied complexity, dimensions, and chemical nature has proven to be particularly challenging.

Nanoparticles are structures useful as carriers for delivering agents with various methods of delivery. Several nanoparticle delivery systems exist, which utilize an array of different strategies to package, transport, and deliver an agent to specific targets. However, a need exists for nanoparticle therapeutics (and methods of making such nanoparticles) that are capable of delivering therapeutic levels of drug to cellular and molecular targets to improve treatment of diseases.

Polynucleotides have important therapeutic applications in medicine. Polynucleotides can be used to modulate (increase or decrease) the expression of genes that are responsible for a particular disease. Gene silencing technology employs polynucleotides that hybridize to a target nucleic acid and modulate gene expression activities or function, such as transcription or translation. Importantly, gene-silencing agents are a promising alternative to traditional small organic compounds that inhibit the function of a protein linked to a disease. RNAseH, small interfering RNAs (siRNAs), microRNAs (miRNAs), and small hairpin RNAs (shRNAs) are examples of gene silencing compounds and mechanisms that prevent the formation of proteins by gene silencing.

A need persists for delivery systems and therapeutic agents that are capable of specifically modulating gene expression to improve treatment of diseases.

BRIEF SUMMARY OF THE INVENTION

Provided herein are non-viral nanoparticles and related compositions, methods, and systems that can be used for carrying and delivering a wide range of molecules of various sizes, dimensions, and chemical natures, including to predetermined targets. One having skill in the art, once armed with this disclosure, will be able, without undue experimentation, to identify, prepare, and exploit non-viral nanoparticles for these and other uses.

In one aspect, the invention provides a system for the delivery of therapeutics, vaccines, and/or diagnostic agents to a desired target. When nanoparticles are formulated with sterile water, such as in the course of developing or manufacturing a pharmaceutically acceptable therapeutic nanoparticle, and a lithium dopant that has been pre-treated with cesium, significant benefits and unexpected advantages are achieved. Such significant benefits and unexpected advantages include, but are not limited to, greater stability of the nanoparticles, including increased capabilities for reliable transport of the nanoparticles, more flexibility and efficiency in employing the disclosed nanoparticles in drug development, such as manufacturing at multiple sites, and other advantages evident to the person of ordinary skill in the art.

The compositions and methods disclosed herein demonstrate the flexibility of the inventive nanoparticles to successfully accommodate ligands and cargoes of choice. In one embodiment, the nanoparticle comprises a core comprised of a bioactive agent including, for example, a drug, vaccine, and/or diagnostic agent, with an optional condensing agent; a surfactant substantially surrounding the core to form a surfactant-coated complex, wherein the surfactant has an hydrophile-lipophile balance (HLB) value of less than about 6.0 units; and a shell that non-covalently adheres to and substantially surrounds the surfactant-coated complex, wherein the shell comprises a targeting moiety (ligand), wherein the shell has been formed with a cationic agent comprising lithium pre-treated with cesium. The mean diameter of the nanoparticle is less than about 50 nanometers (i.e., a sub-50 nm particle).

Also disclosed herein are DNA/RNA chimeric single-stranded polynucleotides of up to about 50 nucleotides in length and capable of specifically hybridizing to the corresponding RNA nucleic acid sequence of Casein Kinase 2 (CK2) alpha and DNA/RNA chimeric single-stranded polynucleotides of up to about 50 nucleotides in length and capable of specifically hybridizing to the corresponding RNA sequence of CK2 alpha prime, as well as methods of preparing and using a combination ("mix") of said polynucleotides comprising different sequences to decrease or inhibit expression of CK2 alpha and CK2 alpha prime and inhibit the growth of solid tumors. Non-limiting examples of such polynucleotides include SEQ ID N0:8 against CK2 alpha and SEQ ID N0:9 against CK2 alpha prime.

Additionally disclosed herein are CK2-targeted polynucleotides with backbones modified to substitute the number 2 position from the 5'end to a 2' O-Methylated (2' O-Me) RNA nucleotide. Non-limiting examples of such backbone-modified polynucleotides are provided in Table 2, below.

In another aspect of the invention, combining and incorporating a mix of thus modified, CK2-targeted polynucleotides in a tumor-targeted sub-50 nanometer capsule results in a therapeutic composition of nanoparticles that, upon administration to a subject, significantly reduces or inhibits tumor growth, tumor cell proliferation, and/or inflammation.

Thus, in one aspect, the invention provides a composition comprising nanoparticles, wherein the nanoparticles comprise: at least one bioactive agent, a surfactant having an HLB value of less than 6.0 units, a ligand, and $Li^+$ and $Cs^+$, wherein: i) the at least one bioactive agent and the surfactant form a surfactant micelle core, ii) the ligand forms a shell, and iii) the nanoparticles have an average diameter of less than 50 nanometers. In one embodiment, the ligand forms an exterior shell. In another embodiment, the nanoparticles are prepared using sterile water.

In still another embodiment, the at least one bioactive agent is a polynucleotide. In still another embodiment, the at least one bioactive agent is a plasmid DNA. In yet another embodiment, the $Li^+$ is pre-treated with $Cs^+$.

In another aspect, the invention provides a system for delivering at least one bioactive agent to a target, the system comprising at least one bioactive agent, a surfactant having an HLB value of less than 6.0 units, a ligand, and $Li^+$ pre-treated with $Cs^+$, to be assembled in a nanoparticle to be used to deliver the at least one bioactive agent to the target. In one embodiment, the bioactive agent is a polynucleotide. In another embodiment, the target is a cell within the body of a mammal.

In a further aspect, the invention provides a method of administering at least one bioactive agent to a subject, the method comprising administering to the subject a composition comprising nanoparticles according to the invention.

In still a further aspect, the invention provides a system for administering at least one bioactive agent to a subject, the system comprising at least one bioactive agent, a surfactant having an HLB value of less than 6.0 units, a ligand, and $Li^+$ pre-treated with $Cs^+$, to be assembled in a nanoparticle to be administered to the subject.

In one embodiment of a composition according to the invention, i): the nanoparticles comprise a plurality of polynucleotides, each comprising a 3' RNA portion and a 5' primarily DNA portion, wherein the number 2 position from the 5' end of each polynucleotide is a 2'-OMe-modified RNA, wherein the sequence of more than about 45% and less than about 55%, of more than about 40% and less than about 60%, or of more than about 30% and less than about 70% of the plurality of polynucleotides on average for the composition of nanoparticles comprises SEQ ID NO: 8, and the sequence of the remainder of the plurality of polynucleotides comprises SEQ ID NO: 9, and ii) the ligand is a protein targeting a tenascin receptor. In another embodiment, the ligand targeting a tenascin receptor is tenfibgen.

The phrase "composition comprising nanoparticles" or a similar phrase as used herein refers, without limitation, to a dose, a sample, a formulation, a manufacturing lot, and other compositions of matter comprising the inventive nanoparticles.

In one aspect, the invention provides a polynucleotide comprising a 3' RNA portion and a 5' primarily DNA portion, wherein the number 2 position from the 5' end is a 2'-OMe modified RNA, wherein the polynucleotide comprises up to about 50 consecutive nucleotides of SEQ ID NO:11 and comprises a portion of at least 8 consecutive nucleotides of SEQ ID NO: 8. In another embodiment, the polynucleotide is about 20 nucleotides in length and comprises SEQ ID NO:8.

In another aspect, the invention provides a polynucleotide comprising a 3' RNA portion and a 5' primarily DNA portion, wherein the number 2 position from the 5' end is a 2'-OMe modified RNA, wherein the polynucleotide comprises up to about 50 consecutive nucleotides of SEQ ID NO:12 and comprises a portion of at least 8 consecutive nucleotides of SEQ ID NO: 9. In another embodiment, the polynucleotide is about 20 nucleotides in length and comprises SEQ ID NO:9.

In one aspect, the invention provides a method for treating a patient, comprising administering to the subject a therapeutically effective amount of a composition according to the invention, wherein the patient has been diagnosed with a solid tumor cancer.

In another aspect, the invention provides a method for treating a patient diagnosed with a solid tumor cancer, comprising administering to the patient a therapeutically effective amount of the composition according to the invention, wherein the nanoparticles comprise a plurality of polynucleotides, wherein each of the plurality of polynucleotides comprises a 3' RNA portion and a 5' primarily DNA portion, wherein the number 2 position from the 5' end of the each of the plurality of polynucleotides is a 2'-OMe modified RNA, wherein the sequence of The plurality of polynucleotides comprises either SEQ ID NO: 8 or SEQ ID NO: 9, wherein the percentage of nanoparticles comprising polynucleotides comprising SEQ ID NO: 8 is at least about 10%, about 20%, about 30%, about 40%, about 50%, about 60%, about 70%, about 80%, or about 90%, and the remainder of the nanoparticles comprise polynucleotides comprising SEQ ID NO: 9, wherein the ligand is a protein targeting a tenascin receptor.

In one embodiment, the percentages are determined based upon the relative levels of CK2 alpha enzymes and CK2 alpha prime enyzmes measured in tumor tissue from one or more subjects, optionally compared to relative levels of CK2 alpha and CK2 alpha prime enzymes in a reference tissue and/or cell culture. In another embodiment, the percentages are about 50% nanoparticles comprising SEQ ID NO: 8 and about 50% comprising SEQ ID NO: 9.

In one aspect, the invention provides a method for preparing a composition according to the invention, the method comprising: i) complexing a bioactive agent with a condensing agent to form a condensed bioactive agent; ii) dispersing the condensed bioactive agent into a water-miscible solvent comprising a surfactant with an HLB of less than 6.0 to form a surfactant micelle; iii) adsorbing a ligand to the exterior surface of the surfactant micelle to form a ligand-stabilized particle (a.k.a., ligand particle); and iv) mixing and incubating the ligand particle with $Li^+$ pretreated with $Cs^+$, and sterile water, to form the composition.

Unless otherwise defined, all technical and scientific terms used herein have the same meaning as commonly understood by one of ordinary skill in the art to which this invention belongs. While suitable methods and materials to practice or test the present invention are provided below, the artisan will recognize that other methods and materials similar or equivalent to those described herein can be used in the practice or testing of the present invention. In addition, the materials, methods, and examples iterated herein are illustrative only and not intended to be limiting.

DETAILED DESCRIPTION OF THE INVENTION

Nanoparticles

In one aspect, the invention provides stable nanoparticles for the targeted delivery of bioactive agents to specific tissues and cells. The inventive nanoparticles have a ligand coating or shell and an average diameter of less than 50 nanometers, enabling the delivery of bioactive agent cargo through the biologic barriers of the body and/or to and into a cell or tissue of interest.

As used herein, "sub-50 nm nanoparticles" are generally referred to in the context of a composition of nanoparticles, wherein said nanoparticles comprise (i) a surfactant micelle comprising a bioactive agent and a hydrophobic surfactant and (ii) a shell comprising a ligand, and having an average diameter of less than about 50 nanometers. In certain embodiments, the nanoparticles of a composition according to the present invention have an average diameter of between about 5 and about 50 nanometers, between about 5 and about 40 nanometers, between about 5 and about 30 nanometers, between about 5 and about 20 nanometers, between about 10 and 40 nanometers, between about 10 and 30 nanometers, or between about 10 and 20 nanometers.

As used herein, the term "shell" generally refers to the exterior or outer shell of the nanoparticle and comprises a layer or coating or corona, which surrounds at least a portion of the outer surface of the core surfactant micelle. In one embodiment, the shell comprises one or more ligands. For a given formulation or composition (used interchangeably herein) of nanoparticles, incorporation of insufficient weight of ligand will typically result in non-uniform particles manifested, for example, by irregular drug-aggregates or fused micelles, while excessive weight of ligand will typically result in large masses or loss of spherical or cubical shape manifested, for example, by elongated structures, as determined by analysis, for example, of TEM or AFM micrographs. One having skill in the art, once armed with the instant disclosure, will be able, without undue experimentation, to identify, prepare, and exploit the use of ligands for incorporation in the inventive nanoparticles.

In one aspect, the invention provides a composition comprising nanoparticles comprising a bioactive agent. The artisan will understand that the phrase "a composition comprising nanoparticles comprising (a certain feature, property, etc.)" indicates that a plurality of the nanoparticles of the composition comprise the certain feature, property, etc.

In one embodiment, the nanoparticles are prepared using sterile water. The terms "prepared," "synthesized," "made", "manufactured", and the like are used interchangeably herein. The phrase "nanoparticles (are) prepared using sterile water", as used herein, means that the salt receiving solution used in the synthesis of the inventive nanoparticles is prepared with sterile water. The artisan will understand that the volume of sterile water added at any step or steps in the preparation of the final salt receiving solution comprises, in total, at least 80%, 90%, 95%, 96%, 97%, 98%, 99%, 99.5%, 99.6%, 99.7%, 99.8%, or 99.9% of the total water volume of the final salt receiving solution. In this context, "final salt receiving solution" refers to the solution prior to the addition of ligand-stabilized nanoparticles. Within this framework, other grades of water may be used, for example, as stock solutions for excipients added to the salt receiving solution. It is understood that the phrases "nanoparticles prepared using sterile water" and "salt receiving solution comprising sterile water" contemplate that sterile water accounts for between about 80% and 100% of the total water volume of the final salt receiving solution. "Sterile water", as used in the context of "nanoparticles prepared using sterile water" and "salt receiving solution comprising sterile water" refers to water in which the level of the following metals is no more than about 0.2 parts per million in sum total: aluminum, arsenic, barium, cadmium, chromium, copper, iron, lead, magnanese, nickel, rubinium, sulfur, vanadium, and zinc. In one embodiment, the "sterile water" refers to water in which the level of the following metals is no more than about 0.1 parts per million in sum total: aluminum, arsenic, barium, cadmium, chromium, copper, iron, lead, manganese, nickel, rubinium, sulfur, vanadium, and zinc. In this framework, levels of each metal and the sum of the metals are based on results reported down to the Method Detection Limit (MDL). Metal testing can be performed according to available methods, such as, for example, U.S. Environmental Protection Agency methods 6010 and 6020.

In some embodiments, the use of water of high purity, such as sterile water, is required to meet regulatory standards for pharmaceutical products. In some embodiments, the use of sterile water is desirable to improve control of manufacturing of nanoparticles by reducing levels of contaminants that can alter characteristics of the nanoparticle such as size, shape, stability, and functionality, as determined by, for example, transmission electron microscopy (TEM) or atomic force microscopy (AFM). In some embodiments, the use of sterile water is desirable to improve control of manufacturing nanoparticles by providing a consistent base to which ingredients such as excipients can be added to improve nanoparticle characteristics such as size, shape, stability, and functionality. The ordinarily skilled artisan will also understand that methods and guidelines are available with respect to tests, grades, and uses of water in pharmaceutical research, development, and manufacturing, such as those produced by United States Pharmacopeia and similar organizations.

In one embodiment, the sterile water used is pharmaceutical grade water. In another embodiment, the sterile water is used to prepare pharmaceutically acceptable therapeutic nanoparticles. The phrase "pharmaceutically acceptable" is employed herein to refer to those compounds, materials, compositions, and/or dosage forms that are, within the scope of sound medical judgment, suitable for use in contact with the tissues of subjects without excessive toxicity, irritation, allergic response, or other problem or complication, commensurate with a reasonable benefit/risk ratio. In one embodiment, the sterile water is also used in other steps in the nanoparticle preparation process, such as the solution preparation of any reagent used in assembling the salt receiving solution or in preparing one or more components of the nanoparticles prior to their addition to the salt receiving solution.

In one embodiment, the nanoparticles comprise the ions lithium ($Li^+$) and cesium ($Cs^+$). In another embodiment, the nanoparticles comprise $Li^+$ that has been pre-treated with $Cs^+$. The phrase "$Li^+$ pretreated with $Cs^+$" and similar phrases, as used herein, refer to the pre-mixing or contacting of the $Li^+$ and $Cs^+$ ions prior to associating said pre-mixed or contacted ions with the sterile water volume that has been or will be used to prepare the salt receiving solution. The concentration of $Li^+$ in the pretreatment step should typically be at least 1M. In one embodiment, the concentration is 2M. In one embodiment, the concentration is 3M. In one embodiment, the concentration is between 3M and 5M. In one embodiment, the concentration is 4M. In one embodiment, the concentration is 5M. In one embodiment, the pretreatment of $Li^+$ with ions prior to addition of the $Li^+$ to the salt receiving bath used to form the nanoparticles is limited to the ion $Cs^+$. In said embodiment, it is understood that the limitation of pretreatment ions to $Cs^+$ is contemplated to specifically exclude other ions being added to the premix but is not contemplated to exclude other ions that may be present in the water source used to pretreat $Li^+$ with $Cs^+$. The pre-mixing or contacting of $Li^+$ and $Cs^+$ ions, for the purposes disclosed and contemplated herein, can be readily performed according to methods for combining ions and similar molecules known to the artisan, including simply mixing the ions in desired concentrations in water, for example, sterile water. In one embodiment, $Cs^+$ at about 0.1 µg/1 ml is added to about 4M $Li^+$, at about 2.5 ppb $Cs^+$ to $Li^+$ by weight, in sterile water in a 50 ml tube, and rotated for about 2 minutes. The artisan will understand that the ratio of $Cs^+$ to $Li^+$ used and/or the concentration of the combined ions in, for example, the sterile water in a 50 ml tube, can be routinely varied to manipulate the morphology or stability or some other characteristic of the nanoparticles subsequently produced.

In another embodiment, $Cs^+$ is pre-mixed with $Li^+$ at a ratio of between about 0.1 and about 100 parts per billion (ppb). In yet another embodiment, the pre-mix ratio is between about 0.1 and about 5 ppb. In still another embodiment, the pre-mix ratio is between about 1 and about 4 ppb. Each of these ranges include sub-ranges within that range. For example, between about 1 and about 4 ppb includes such ranges as: between about 1.2 and about 2.5 ppb, and between about 2 and about 4 ppb, and the like. Surprisingly, for nanoparticles prepared using sterile water, those particles formulated with $Cs^+$ pre-mixed with $Li^+$ formed desirable spherical, cuboid, or elliptical sub-50 nanometer nanoparticles, while those particles formulated with $Cs^+$ and $Li^+$ that were simply commingled in the salt receiving solution and not pre-mixed, generally formed unwound, long rod-like compositions unsuitable for use. One having skill in the art, once armed with this disclosure, will be able, through routine experimentation, to identify, prepare, and exploit the use of $Cs^+$ and $Li^+$ pre-mixtures for the targeted nanoparticles.

The disclosed nanoparticles provide a modular targeting component that can be readily synthesized for a given target, for example, a given tissue or cellular target, without the steps of chelating, conjugating, or covalently attaching the targeting moiety to the nanoparticle. One having skill in the art will understand that, with judicious selection of a targeting moiety based upon the intended target and methods and compositions known in the art, the inventive nanoparticles are capable of delivering bioactive agents to predetermined target tissue and cells.

In one embodiment, the shell comprises a ligand. The term "ligand", as used herein, refers to a substance that binds to a target receptor. In some embodiments, the ligand comprises a protein, a peptide, a polypeptide, a carbohydrate, polyvinylpyrrolidone (PVP), an antibody, or a biocompatible polymer, or fragments thereof, or a small molecule. In one embodiment, the sub-50 nm nanoparticles are coated with at least one tissue- or cell-specific ligand. A "coated nanoparticle" refers to a nanoparticle wherein the ligand is bound to the core surfactant micelle via a non-covalent association. The flexibility of ligand options for the inventive nanoparticles is enabled, in part, by the absence of such complex steps as attaching the ligand to the nanoparticle via chelation, conjugation, or covalent attachment, employing, instead, a straight-forward step of adsorbing the ligand to the hydrophobic micelle surface, and, subsequently, stabilizing the targeted particle in a salt crystallization solution. Thus for example, adsorption of the ligand to the core surfactant micelle allows for more efficient incorporation of larger ligands than nanoparticles where ligands are conjugated or chelated to the core particle. Diverse ligands including, for example, tenfibgen, hyaluronan, and synthetic polymers such as PVP, may be utilized as ligands in formulating the inventive $Cs^+$-treated nanoparticles. For example, a particle comprising PVP would be formulated similarly to Formula J (Examples, below) for a 5.5 kb plasmid except using 4 µl of 25 kD PEI as a condenser, 3.3 µg of 10 kD PVP as a ligand adsorbed to the core micelle, and modifying the receiving bath to 1.5 nM $Mg^{2+}$ and 1.88 nM $Sr^{2+}$, all other ions the same.

In one embodiment, the ligand targets cells with tenascin receptors. In another embodiment, the ligand is tenfibgen.

In still another embodiment, the ligand is hyaluronan.

In one aspect, the invention provides a system to deliver a bioactive agent to a target or to administer a bioactive agent to a subject. In one embodiment, the system comprises at least one bioactive agent, for example, a polynucleotide, a surfactant having an HLB value of less than 6.0 units, a ligand, and $Li^+$ and $Cs^+$, to be assembled in a sub-50 nanometer nanoparticle to be used to deliver the at least one bioactive agent to the target or administer the at least one bioactive agent to a subject. The term "system", as used herein, refers to a formulation or composition that enables the introduction of a bioactive agent in the body of a subject and improves its efficacy or performance.

In one embodiment, the instant nanoparticles incorporate a bioactive agent or agents useful for modulating gene expression, to increase or decrease the production of specific gene products (e.g., proteins or RNA). In another embodiment, the bioactive agent or agents engage(s) mechanisms of action such as RNaseH, RNAi, and dsRNA enzymes, as well as other modulating mechanisms based on target degradation or target occupancy.

Bioactive Agents

Cs-treated nanoparticles of the present invention can be used to carry and deliver bioactive agents to targeted tissues and cells. The phrase "bioactive agent" or "bioactive agents", as used herein, refers to one or more agents that, when administered or delivered to a cell, tissue, or organism, mimics, alters, or modulates one or more physiological, biochemical, or pathological processes of the cell, tissue, or organism. Preferably, the alteration or modulation is a medically desirable alteration or modulation. More specifically, a bioactive agent can be any one or more of a number of different compounds or molecules for purposes comprising imaging or monitoring or therapeutic or prophylactic uses including, but not limited to, a bioactive agent such as an oligonucleotide, a polynucleotide, a plasmid DNA, any nucleic acid-based molecule including but not limited to DNA, RNA, siRNA, mRNA, miRNA, shRNA, aptamers, antisense molecules, or ribozymes, as well as a protein, a polypeptide, a peptide, a carbohydrate, an antibody or a small molecule.

Without wishing to be bound by theory, the flexibility of bioactive agent options is enabled, in part, by the partitioning and condensing features of the hydrophobic-surfactantcoated micelle that forms the core of the nanoparticle. The artisan would recognize these features as being suitable and functional for the purposes of formulating the inventive nanoparticles with oligonucleotides, polynucleotides, plasmid DNA, any nucleic acid-based molecule including DNA, RNA, siRNA, miRNA, shRNA, aptamers, antisense molecules, or ribozymes, proteins, polypeptides, peptides, carbohydrates, antibodies, or other cargoes, more preferably, but not exclusively, hydrophilic and/or negatively or approximately neutrally charged cargoes. This flexibility of the inventive nanoparticles for incorporating a range of bioactive agents in different formulations is demonstrated, for example, by the formulation of a 10.5 kb plasmid DNA and hyaluronan nanoparticle shell with a resulting average diameter of 22.7 nanometers and charge of −6.4 mev, and the formulation of a 6800 dalton single strand oligonucleotide and tenfibgen nanoparticle shell with a resulting diameter of 19.5 nanometers and charge of −5.8 mev (see Examples).

Thus, other diverse bioactive agents can be incorporated in the cesium-pretreated nanoparticles through routine experimentation. For example, the small molecule erythritol (MW, 122) would be formulated similar to Formula A (Examples), except that 500 μg of erythritol without any condenser would be micellized with 8.75 μg of surfactant, coated with 5.5 mcg of TBG, and atomized into a receiving bath modified with 6.25 nM of $Mg^{2+}$ and 9.38 nM of Sr2+, all other ions the same. Resulting nanoparticle size would be approximately 25 nm in diameter, and surface charge would be approximately −12 mev.

The phrase "hydrophobic surfactant-coated", as used herein, refers to the coating or layer of hydrophobic surfactant used to form the surfactant micelle, and which surrounds at least a portion of the bioactive agent and optional condensing agent. For a given formulation, incorporation of insufficient surfactant will typically result in irregular drug aggregates, while excessive surfactant will typically result in surfactant globules, as determined by analysis for example of TEM or AFM micrographs. In certain embodiments, the bioactive agent is a single-stranded chimeric oligonucleotide. Bioactive agents including oligonucleotides can generally be prepared using techniques well known in the art but can also be obtained from commercial manufacturers.

In one embodiment, the bioactive agent is a plurality of bioactive agents against a molecular target. In another embodiment, the bioactive agent comprises a mix of two or more bioactive agents with different molecular targets and/or mechanisms of action.

In some embodiments, the bioactive agent is condensed with a cationic condensing agent comprising polyethyleneimine, polyornithine, polyarginine, spermine, or other cationic condensing agent or agents well known in the art.

"Specifically hybridizable" and "complementary" are terms that are used to indicate a sufficient degree of complementarity such that stable and specific binding occurs between a polynucleotide of the present invention and a target RNA molecule. It is understood in the art that the sequence of a polynucleotide need not be 100% complementary to that of its target RNA molecule to be specifically hybridizable. One of ordinary skill in the art would recognize that the compounds provided herein are at least 80%, at least 85%, at least 90%, at least 95%, at least 96%, at least 97%, at least 98%, at least 99% or 100% complementary to a target nucleic acid. A polynucleotide is specifically hybridizable when (a) binding of the polynucleotide to the target RNA molecule interferes with the normal function of the target RNA molecule, and (b) there is sufficient complementarity so that binding of the polynucleotide to the target RNA molecule is highly selective and largely avoids non-specific binding of the polynucleotide to non-target sequences under conditions in which specific binding is desired, i.e., under conditions in which in vitro assays are performed or under physiological conditions for in vivo assays or therapeutic uses. Examples of methods for designing oligonucleotides that are sufficiently complementary to be useful in the present invention and such design skills are within the purview of one of skill in the art.

The term "RNA" or "RNA molecule" or "ribonucleic acid molecule" refers to a polymer of ribonucleotides. "Target RNA" refers to any RNA that can hybridize with a sufficiently complementary polynucleotide of the present invention. Target RNA can include, without limitation, pre-mRNA, pre-miRNA, pri-miRNA, mRNA, miRNA, small nuclear or cytosolic non-coding regulatory RNAs, ribosomal RNA, transfer RNAs, hnRNA at any stage in the mRNA processing pathway, or mitochondrial RNAs. "mRNA" or "messenger RNA" is single-stranded RNA that specifies the amino acid sequence of one or more polypeptide chains. In one embodiment, the target mRNA of the invention specifies the amino acid sequence of a cellular protein (e.g., a nuclear, cytoplasmic, mitochondrial, transmembrane, or membrane-associated protein). In another embodiment, the target mRNA of the invention specifies the amino acid sequence of an extracellular protein (e.g., an extracellular matrix protein or secreted protein). The term "DNA" or "DNA molecule" or "deoxyribonucleic acid molecule" refers to a polymer of deoxyribonucleotides.

The term "nucleic acid molecule" or "polynucleotide" refers to any nucleic acid-containing molecule, including, but not limited to, DNA and/or RNA of more than 1 nucleotide in either single chain, duplex, or multiple chain form. The terms encompass sequences that include any of the known base analogs of DNA and RNA. The term "polynucleotide" is also meant to encompass polydeoxyribonucleotides containing 2'-deoxy-D-ribose or modified forms thereof, RNA and any other type of polynucleotide that is an N-glycoside or C-glycoside of a purine or pyrimidine base, or modified purine or pyrimidine base or basic nucleotide. The polynucleotide, in some embodiments, may encode promoter regions, operator regions, structural regions, termination regions, combinations thereof, or any other genetically relevant material that regulates or modifies chromatin or other polynucleotides. Similarly, the term "genetic" as used herein, refers to any material capable of modifying gene expression.

The term "oligonucleotide" refers to a short length of single-stranded polynucleotide chain. Oligonucleotides are typically less than 200 residues long (e.g., between about 8 and 100). The terms "polynucleotide" and "oligonucleotide" are used interchangeably herein.

As used herein, "gene silencing," "gene silencing molecule," "gene silencing compound", and the like refer to a polynucleotide, at least a portion of which is at least partially complementary to a target nucleic acid to which it hybridizes. In certain embodiments, a gene silencing compound modulates (for example, decreases) expression or amount of a target nucleic acid. In certain embodiments, a gene silencing compound alters splicing of a target pre-mRNA, resulting in a different splice variant. In certain embodiments, an antisense compound modulates expression of one or more different target proteins. Gene silencing mechanisms contemplated herein include, but are not limited to, RNase H mechanisms, RNAi mechanisms, splicing modulation, translational arrest, altering RNA processing, inhibiting microRNA function, and mimicking microRNA function, as well as additional mechanisms identifiable by the artisan upon reading of the present disclosure.

The term "small interfering RNA" ("siRNA") (also referred to in the art as "short interfering RNAs") refers to an RNA (or RNA analog) comprising between about 10-50 nucleotides (or nucleotide analogs) capable of directing or mediating RNA interference. As used herein, the term "RNA interference" ("RNAi") refers to a selective intracellular degradation of RNA. In some embodiments, the bioactive agent is a double-stranded siRNA polynucleotide.

As used herein, "expression" refers to the process by which a gene ultimately results in a protein. Expression includes, but is not limited to, transcription, splicing, post-transcriptional modification, and translation.

The term "gene" refers to a nucleic acid (e.g., DNA) sequence that comprises coding sequences necessary for the production of a polypeptide, precursor, or RNA (e.g., rRNA, tRNA, and other ncRNAs). The polypeptide can be encoded by a full length coding sequence or by any portion of the coding sequence, so long as the desired activity or functional properties (e.g., enzymatic activity, ligand binding, signal transduction, immunogenicity, etc.) of the full-length or fragment is retained.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "inhibition of gene expression" refers to conditions where a polynucleotide of the present invention hybridizes to a target RNA and provides partial or complete loss of function of said gene. It is understood that a polynucleotide need not be 100% complementary to its target RNA sequence to be specifically hybridizable. In certain embodiments, a reduction of target gene expression by at least about 10%, 25%, 50%, 60%, 70%, 80%, 90%, 95%, or 99% is desired relative to the level of expression in the absence of the bifunctional chimeric single stranded polynucleotides of the present invention. The present invention is not limited to the inhibition of expression of a particular gene.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides, and in one embodiment of the present invention, are joined together by a phosphodiester linkage between 5' and 3' carbon atoms of the sugar moiety.

The term "nucleotide analog" or "altered nucleotide" or "modified nucleotide" refers to a less commonly occurring nucleotide, including natural and non-naturally occurring ribonucleotides or deoxyribonucleotides. Nucleotide analogs may be modified at any position so as to alter certain chemical properties of the nucleotide yet retain the ability of the nucleotide analog to perform its intended function. Nucleotide analogs may also comprise modifications to the sugar portion of the nucleotides. The phosphate group of the nucleotide may also be modified, e.g., by substituting one or more of the oxygens of the phosphate group with sulfur (e.g., phosphorothioates), or by making other substitutions which allow the nucleotide to perform its intended function.

For use in preparing the nucleoside structural subunits of the compounds of the invention, suitable nucleobases for incorporation in these nucleoside subunits include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch, et al. 1991 *Angewandte Chemie*, International Edition 30:613, all incorporated herein by reference.

"Phosphodiester" refers to a polynucleotide with an oxygen atom linking consecutive nucleotides. "Phosphorothioate" refers to a polynucleotide in which the oxygen atom normally linking two consecutive nucleotides has been replaced with sulfur and which resists degradation by cellular enzymes. Polynucleotides of the present invention have their nucleoside subunits connected by phosphorus linkages from a list including phosphodiester, phosphorothioate, 3'-(or -5')deoxy-3'-(or -5')thio-phosphorothioate, phosphorodithioate, phosphoroselenates, 3'-(or -5')deoxy phosphinates, borano phosphates, 3'-(or -5')deoxy-3'-(or 5'-) amino phosphoramidates, hydrogen phosphonates, borano phosphate esters, phosphoramidates, alkyl or aryl phosphonates and phosphotriester phosphorus linkages. Phosphorothioate modification of nucleoside linkages for increased stability has been reported to minimally effect silencing activity (2007 *Nat Rev Mol Cell Biol* 8:23-6). In one embodiment, a backbone comprising PS/2-O-Me may be of value in situations where PO/2-O-Me seems limited.

The term "phosphorylated" means that at least one phosphate group is attached to a chemical (e.g., organic) compound. Phosphate groups can be attached, for example, to proteins or to sugar moieties via the following reaction: free hydroxyl group+phosphate→donor phosphate ester linkage. Also intended to be included within the scope of the instant invention are phosphate group analogs, which function in the same or similar manner as the mono-, di-, or triphosphate groups found in nature. In one embodiment, the chimeric polynucleotides disclosed herein comprise extrinsic 5' phosphorylation. In another embodiment, the chimeric polynucleotides disclosed herein do not comprise extrinsic 5' phosphorylation. The term "extrinsic 5' phosphorylation" generally refers to phosphorylation carried out through synthetic methods and not natural biological processes.

"Chimeric" refers, but is not limited, to a molecule that is composed of both RNA and DNA moieties that are naturally occurring or nucleotide analogs, linked by phosphodiester, phosphorothioate, and/or any other naturally occurring or synthetic linkage that permits the nucleotides or analogs to retain their intended function. The oligonucleotide or polynucleotide can be referred to as having at least two segments. One segment is defined as the portion beginning at the 3' end of the polynucleotide and is the ribonucleic acid segment and should include at least about three consecutive ribonucleotides, and the second segment is defined as the portion ending at the 5' end of the polynucleotide and is the primarily deoxyribonucleic acid portion, and comprises at least about 6, 7, 8, 9, or 10 deoxyribonucleotides, wherein a total of zero, one, two, or three riboncucleotides may be placed between the at least about 6, 7, 8, 9, or 10 deoxyribonucleotides. In one embodiment, the second section comprises at least 5 consecutive deoxyribonucleotides. In one embodiment, the number 2 position from the 5' end is a 2'-OMe modified RNA.

Preferred single stranded chimeric polynucleotides in accordance with this invention preferably comprise from about 8 to about 50 nucleoside subunits. In the context of this invention, it is understood that this encompasses non-naturally occurring oligomers as hereinbefore described, having 8 to 50 nucleoside subunits. It is more preferred that the single stranded chimeric polynucleotides of the present invention comprise from about 15 to about 25 nucleoside subunits. Accordingly, single stranded chimeric polynucleotides can be 8 nucleotides in length, 9 nucleotides in length, 10 nucleotides in length, 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, 30 nucleotides in length, 31 nucleotides in length, 32 nucleotides in length, 33 nucleotides in length, 34 nucleotides in length, 35 nucleotides in length, 36 nucleotides in length, 37 nucleotides in length, 38 nucleotides in length, 39 nucleotides in length, 40 nucleotides in length, 41 nucleotides in length, 42 nucleotides in length, 43 nucleotides in length, 44 nucleotides in length, 45 nucleotides in length, 46 nucleotides in length, 47 nucleotides in length, 48 nucleotides in length, 49 nucleotides in length, or 50 nucleotides in length. As will be appreciated, a "nucleoside subunit" is a nucleobase and sugar or sugar surrogate combination suitably bound to adjacent subunits through phosphorus linkages in oligoribonucleotides and through non-phosphorus linkages in oligoribonucleosides. In this context, the term "nucleoside subunit" is used interchangeably with the term "nucleoside unit" or "nucleoside." More preferably, the chimeric oligonucleotides of the invention will have nucleosides linked by naturally occurring phosphodiester linkages.

In certain embodiments, the bioactive agent is a single-stranded polynucleotide, and the polynucleotide is a guide strand, garnered from standard optimization siRNA techniques. A discussion of conventional siRNA sequence selection is included herein.

The target RNA cleavage reaction guided by siRNAs is highly sequence-specific. In general, siRNA containing a nucleotide sequence identical to a nucleotide sequence or a portion of a nucleotide sequence of the target gene is preferred for inhibition. However, 100% sequence identity between the siRNA and the target gene is not required to practice the present invention. Thus, the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of the siRNA contribute equally to target recognition. Mismatches in the center of the siRNA are most critical and essentially abolish target RNA cleavage. In contrast, the 3' nucleotides of the siRNA do not contribute significantly to specificity of target recognition. In particular, residues 3' of the siRNA sequence, which is complementary to the target RNA (e.g., the guide sequence), are not critical for target RNA cleavage.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment is generated over a certain portion of the sequence aligned having sufficient identity, but not over portions having low degree of identity (i.e., a local alignment). A preferred, non-limiting example of a local alignment algorithm utilized for the comparison of sequences is the algorithm of Karlin and Altschul ((1990) Proc. Natl. Acad. Sci. USA 87:2264-68, modified as in Karlin and Altschul (1993) Proc. Natl. Acad. Sci. USA 90:5873-77, incorporated herein by reference. Such an algorithm is incorporated into the BLAST programs (version 2.0) of Altschul, et al. (1990) J. Mol. Biol. 215:403-10), incorporated herein by reference.

In another embodiment, the alignment is optimized by introducing appropriate gaps, and percent identity is determined over the length of the aligned sequences (i.e., a gapped alignment). To obtain gapped alignments for comparison purposes, Gapped BLAST can be utilized as described in Altschul, et al., ((1997) Nucleic Acids Res. 25(17):3389-3402). In still another embodiment, the alignment is optimized by introducing appropriate gaps, and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

Sequence identity of at least about 80%, at least about 85%, at least about 90%, at least about 95%, at least about 96%, at least about 97%, at least about 98%, at least about 99% or about 100% between the siRNA and a portion of the target gene is preferred. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm((° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Treatment Methods

In one aspect, the invention provides a method of inhibiting the expression of casein kinase 2 in a solid tumor. This inventive method comprises administering targeted nanoparticles delivering polynucleotides to the tumor, wherein the polynucleotides hybridize to casein kinase 2 nucleic acid sequences and reduce or inhibit the expression thereof.

In one aspect, the invention provides a method of modulating activity of downstream targets of casein kinase 2 in a solid tumor. In some embodiments, downstream targets of casein kinase 2 include, without limitation, NF-$_\kappa$B p65, Cdc37, and AKT. This inventive method comprises administering targeted nanoparticles delivering polynucleotides to the tumor, wherein the polynucleotides hybridize to casein kinase 2 nucleic acid sequences and reduce or inhibit the activity of downstream targets, and/or downstream markers of casein kinase 2 activity, including, for example, Ki-67.

In another aspect, the invention provides a method of reducing the size of a solid tumor or inhibiting or stabilizing the growth of a solid tumor in a subject. This inventive method comprises administering targeted nanoparticles delivering polynucleotides to the tumor, wherein the polynucleotides hybridize to casein kinase 2 nucleic acid sequences and reduce or inhibit the expression thereof. In certain embodiments, targeted nanoparticles delivering polynucleotides to the tumor result in reduction in size or stabilization or inhibition of growth of the solid tumor.

As used herein, the term "subject" refers to any animal (e.g., a mammal), including, but not limited to, humans, non-human primates, vertebrate animals, rodents, and the like, which is to be the recipient of a particular treatment. The terms "subject", "patient", and "individual" are used interchangeably herein.

In some embodiments, the target is an in vitro biological system such as in vitro tissues or cells, and the method comprises contacting the target with the nanoparticles herein described.

In one embodiment, oligonucleotides for binding to casein kinase 2 have the sequence shown in SEQ ID NO:8 (for the target casein kinase 2 alpha), or SEQ ID NO:9 (for the target casein kinase 2 alpha prime). In one embodiment of a composition of nanoparticles according to the invention, the nanoparticles comprise a plurality of polynucleotides, wherein the percentage of the plurality of polynucleotides that comprises SEQ ID NO: 8 is, on average, more than about 1% and less than about 100%, more than about 30% and less than 70%, more than about 40% and less than about 60%, more than about 45% and less than about 55%, more than about 48% and less than about 52%, more than about 49% and less than about 51%, or is about 50%, and the remainder of the plurality of polynucleotides comprises SEQ ID NO:9. Factors influencing the percentages of each polynucleotide sequence include, for example, the relative volume of each polynucleotide incorporated upon formulating the nanoparticles or the relative encapsulation percentage of each polynucleotide. The polynucleotide makeup of the composition can be determined using sampling methods known in the art, such as hybridization assays and functional cell assays.

In one embodiment of a composition of nanoparticles according to the invention, a mix of nanoparticles comprises polynucleotides comprising either SEQ ID NO: 8 or SEQ ID NO: 9. In another embodiment of a nanoparticle composition according to the invention, the percentage of nanoparticles that comprise polynucleotides comprising SEQ ID NO: 8 is about 10%, about 20%, about 30%, about 40%, about 50%, about 60%, about 70%, about 80%, or about 90%, with the remainder of nanoparticles of the composition comprising polynucleotides comprising SEQ ID NO: 9.

Representative tumors contemplated for treatment by methods of the invention include those associated with certain cancers, and include, without limitation, breast cancer, lung cancer (including non-small cell lung carcinoma), prostate cancer, colorectal cancer, brain cancer, esophageal cancer, kidney cancer, bladder cancer, pancreatic cancer, cervical cancer, head and neck cancer, skin cancers, nasopharyngeal carcinoma, liposarcoma, epithelial carcinoma, renal cell carcinoma, gallbladder adenocarcinoma, parotid adenocarcinoma, ovarian cancer, melanoma, lymphoma, glioma, and endometrial sarcoma.

In one embodiment, treatment by methods of the invention includes administration to patients diagnosed with a solid tumor cancer. "Solid tumor", as used herein, refers to an abnormal mass of tissue that results from the proliferation of cells. Solid tumors can arise in any part of the body and may be benign (not cancerous) or malignant (cancerous). Most types of cancer other than leukemias can form solid tumors. Solid tumors include, without limitation, adenocarcinomas, carcinomas, hemangiomas, liposarcomas, lymphomas, melanomas, and sarcomas. The phrase "solid tumor" can also be used to refer to conditions such as endometriosis, i.e., conditions caused by uncontrolled proliferation of cells.

Tenascin is a large glycoprotein shown to be overexpressed in the microenvironment of solid tumors (Brellier, et al. 2011 *J Cell Molec Med* 16: 32-40). Receptors for tenascin are found on tumor cells, representing an attractive target for treating solid tumor cancers by employing therapeutic nanoparticles with tenascin-directed ligands. Non-limiting examples of receptors for tenascin found on tumor cells include integrin alpha V, alpha 2, beta 1, and beta 3. One having skill in the art, once armed with this disclosure, will be able, without undue experimentation, to identify, prepare, and exploit tenascin-directed ligand nanoparticles to solid tumors for the purposes of targeting and delivering bioactive agents to solid tumors. Non-limiting examples of such tenascin-directed ligands include tenascin-C, tenascin-W, and fragments thereof, including, but not limited to, tenfibgen.

In one embodiment, the inventive nanoparticle compositions are useful for treating any condition in which inhibiting expression of a target gene is potentially of use. In another embodiment, the compositions may be used for treating a subject suffering from a proliferative disease. By "proliferative disease" is meant any human or animal disease or disorder affecting any one or any combination of organs, cavities, or body parts, which is characterized by single or multiple local abnormal proliferations of cells, groups of cells, or tissues, whether benign or malignant.

The terms "treatment", "treating", and the like are intended to mean administering a therapeutic, vaccine, or diagnostic on one or more occasions for the purpose of obtaining or assessing a desired pharmacologic and/or physiologic effect in a subject. The effect may be prophylactic in terms of completely or partially preventing a disease or symptom thereof and/or may be therapeutic in terms of a partial or complete cure for a disease and/or adverse effect (symptom) attributable to the disease. "Treatment", as used herein, covers any treatment of a disease in a subject and includes, without limitation: (a) preventing a disease or condition from occurring in an individual who may be predisposed to the disease but has not yet been diagnosed as having it; (b) eliminating or inhibiting the disease, (e.g., arresting its development); or (c) relieving the disease (e.g., reducing or eliminating symptoms associated with the disease).

In another aspect, the invention provides a single-stranded (ss) oligonucleotide of up to about 50 nucleotides in length that includes a portion of at least 8 consecutive nucleotides of SEQ ID NO: 8, wherein the ss oligonucleotide inhibits the expression of human casein kinase 2 alpha. In another aspect, the invention provides a ss oligonucleotide of up to about 50 nucleotides in length that includes a portion of at least 8 consecutive nucleotides of SEQ ID NO: 9, wherein the ss oligonucleotide inhibits the expression of human casein kinase 2 alpha prime.

Administration

The formulation of therapeutic compositions of the present invention and their subsequent administration are described herein and can be practiced by those of ordinary skill in the art. In general, for therapeutics, a patient in need of therapy is provided a composition in accordance with the invention, in dosages and novel regimen strategies as described elsewhere herein. In some embodiments of the present invention, administration is determined based upon one or more of the patient's body weight or surface area, age, and severity of the disease or disorder being treated.

In one embodiment, the subject is treated with the nanoparticle composition, for example, comprising polynucleotides, at a dose/in an amount sufficient to reduce, stabilize, or inhibit expression of a target gene against a suitable control. In another embodiment, the subject is treated with the single-stranded polynucleotide at a dose/in an amount sufficient to reduce, stabilize, or inhibit the target lesion against a suitable control. In another embodiment, the bioactive agent (for example, polynucleotide) dose is of equal to or less than about 20 mg/kg body weight, less than about 10 mg/kg body weight, or less than about 5 mg/kg body weight. In other embodiments, the bioactive agent, for example, a single-stranded chimeric polynucleotide, is delivered at a dose of less than about 4 mg/kg body weight, less than about 3 mg/kg body weight, less than about 2 mg/kg body weight, less than about 1 mg/kg body weight, less than about 100 µg/kg body weight, less than about 100 nanogram(ng)/kg body weight, less than about 10 ng/kg body weight, less than about 1 ng/kg body weight, less than about 100 picogram(pg)/kg body weight, less than about 10 pg/kg body weight, less than about 1 pg/kg body weight, less than about 100 femtogram(fg)/kg body weight, less than about 10 fg/kg body weight, less than about 1 fg/kg body weight, less than about 100 attogram(ag)/kg body weight, less than about 10 ag/kg body weight, or less than about 1 ag/kg body weight. Similar dosage ranges can be developed and used based upon for example the body surface area of the subject.

The treatment regimen may last for a period of time that will vary depending upon the nature of the particular disease, its severity, and the overall condition of the patient, and may extend from once daily to once every 30 years. Following treatment, the patient may be monitored for changes in his/her condition and for alleviation of the symptoms of the disease or disorder state. The dosage of the bioactive agent may either be increased in the event that the patient does not respond significantly to current dosage levels, or the dosage may be decreased if an alleviation of the symptoms of the disease or disorder is observed, or if the disease or disorder has been ablated.

Dosing is dependent on severity and responsiveness of the disease condition to be treated, with the course of treatment lasting from several days to several months, or until a cure is effected or a diminution of disease or disorder is achieved. Optimal dosing schedules can be calculated, for example, from measurements of bioactive agent accumulation in the body of the patient. Persons of ordinary skill can readily determine optimum dosages, dosing methodologies, and repetition rates. Optimum dosages may vary depending on the relative potency of individual compounds, and can generally be estimated, for example, based on EC50 found to be effective in in vitro and in vivo animal models. Dosages may be given, for example, once or more daily, weekly, monthly or yearly, or even once every 2 to 30 years.

In some embodiments, methods of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to administering a composition of nanoparticles as described herein. For example, a transcription rate, mRNA level, translation rate, protein level, biological activity, lesion size, cellular characteristic or property, genotype, phenotype, etc. can be determined prior to introducing a composition of nanoparticles of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

In another aspect, the invention provides methods of treatment comprising administering to a subject in need thereof a therapeutically effective amount of a bioactive agent in a formulated composition of nanoparticles according to the invention. By the term "therapeutically effective amount", for example, of a bioactive agent, is meant such amount as is capable of obtaining the desired phenotype or performing the desired therapeutic function such as stabilizing, slowing, reducing, eliminating, or preventing a disease or disorder (or a symptom of such disease or disorder). The exact amount required will vary, depending on known variables, such as the bioactive agent employed, the condition of the subject, and the parameters of the therapeutic regimen. Thus, it is neither necessarily possible nor required to specify an exact "therapeutically effective amount." Rather, the appropriate effective amount may be determined by one of ordinary skill in the art using routine experimentation.

The compositions of the present invention may be administered via a number of routes, depending upon whether local or systemic treatment is desired and upon the area to be treated. Administration may be topical (including ophthalmic, vaginal, rectal, intranasal, transdermal), oral, or parenteral. Parenteral administration includes, but is not limited to, intravenous, subcutaneous, intraperitoneal or intramuscular injection, intratumoral, or intrathecal or intraventricular administration. Without wishing to be bound by theory, the flexibility of particle (composition) administration options is enabled, in part, by the small size and low surface charge of the highly stable nanoparticles of the inventive composition, allowing the particle and its drug cargo to traverse biologic barriers and size-limited structures such as the bloodstream wall, lymphatic channels, and the skin to reach cellular and molecular targets.

"Low surface charge" of the nanoparticles of the inventive compositions generally means an average surface charge of between about −20 and about +4 milli-electron volts (mev), although one skilled in the art will understand that the inventive nanoparticles having an average surface charge outside of this range can still be exploited for therapeutic purposes, if the nanoparticles retain their spherical or elliptical shape, sub-50 nanometer size, and crystallized form.

In one embodiment, the invention provides a method of treating a disease or disorder in a subject, for the purpose of obtaining a desired phenotype or performing a desired function such as stabilizing, slowing, reducing, or eliminating such disease or disorder (or a symptom of such disease or disorder), such as, without limitation, proliferative disease, such as, without limitation, cancer, comprising administering to a subject under conditions suitable for the treatment of the disease or disorder, a therapeutically effective amount of a nanoparticle composition, wherein the nanoparticles comprise a micelle core comprising bioactive agents comprising a mix of SEQ ID NO: 8 and SEQ ID NO: 9, a surfactant with an HLB value of less than or equal to about 6.0, a shell adsorbed to the micelle core and comprising tenfibgen, $Li^+$ and $Cs^+$, and having a mean diameter of less than about 50 nanometers, wherein the nanoparticles are administered via one or more of the routes described above. In another embodiment, the inventive method comprises pre-treatment of the $Li^+$ with $Cs^+$. In one embodiment, the polynucleotide of the present invention may be introduced in an amount which allows delivery of at least about 1, 5, 10, 50, 100, 500, or 5000 polynucleotides per target cell.

The following illustrates some of the benefits and advantages of the instant invention based on work described in the examples, below. Stable tenfibgen-shell sub-50 nanometer nanoparticles made with sterile water and Cs+ pre-mixed with Li+, and encapsulating a mix of oligonucleotides comprising 2R-modified anti-CK2 SEQ ID NO: 8 and SEQ ID NO: 9, significantly inhibited tumor growth in mice over a 30-day period (Table 3, below). An analysis of the tumors treated with the mix also showed significant inhibition of Ki-67, a marker of cell proliferation, and NF-kB, a marker of inflammation. Under similar experimental conditions, mice treated with only nanoencapsulated 2R-modified SEQ ID NO: 8 showed reductions in tumor weight and NF-kB vs. controls, but the changes were not significant, and the Ki-67 index for the treated group increased vs. controls. Similarly, mice treated with only a nanoencapsulated, unmodified oligonucleotide mix (SEQ ID NO: 5 and SEQ ID NO: 6) showed an increase in tumor weight, with small changes in Ki-67 and NF-kB.

Preparation of Nanoparticles

The following description of methods that can be used to make targeted sub-50 nanoparticles is meant to be representative only and is not meant to be limiting. U.S. Pat. Nos. 6,632,671, 7,741,304, and U.S. Patent Publication No. 2013/0267577, incorporated herein by reference, disclose the preparation of unmodified nanoparticles. Briefly, a negatively-charged bioactive agent such as a nucleic acid that is to be targeted and delivered to, for example, a tumor cell, can be complexed with a polycationic polymer to condense or reduce its size to about 50 nm or less. A number of different polycationic polymers (also known as "condensing" agents or proteins) can be used and are well-known in the art (Rolland 1998, Crit. Rev. Therapeutic Drug Carr. Syst., 15:143-198). For example, enough polycationic condensing protein can be complexed with the negatively-charged cargo moiety to neutralize at least about 75% (e.g., about 80%, 85%, 90%, 95%, 99% or 100%) of the negatively-charged cargo moiety, which, for nucleic acids, can be measured by ethidium dye exclusion (see, for example, (1998, J. Controlled Release, 53:289-99)). Simply by way of example, 125 μg of 10 kD polyornithine can be used to condense 500 μg of a 20-mer oligonucleotide, or 87.5 μg of spermine may be used to condense 250 μg of a 14 kD siRNA oligo. For cargo moieties lacking a negative charge or bearing a positive charge, a condensing polycationic polymer may not be necessary.

An aqueous solution of the complexed or uncomplexed cargo moiety can be encapsulated by first dispersing the cargo moiety into a biocompatible, water-miscible solvent using a biocompatible, water-insoluble surfactant system suitable for preparation of an inverted or reverse micelle. Suitable surfactant systems are well-known in the formulation arts as amphiphilic materials that are essentially hydrophobic and characterized by a hydrophile-lipophile balance (HLB) of less than about 6, a critical micelle concentration (CMC) of less than about 200 μM, or a critical packing diameter greater than 1. In some embodiments, the HLB is less than about 5. Hydrophobic surfactants and hydrophobic, water-miscible solvents suitable for preparing reverse micelles are described in Pashley & Karaman (2004, In Applied Colloid and Surface Chemistry, John Wiley, pp. 60-85), Rosen (2004, in Surfactants and Interfacial Phenomena, John Wiley), The Handbook of Industrial Surfactants (1993, Ash, ed., Gower Pub), and Perry's Chemical Engineer's Handbook (1997, Perry & Green, 7th Ed., McGraw-Hill Professional), incorporated herein by reference.

In some embodiments, the surfactant component may be 2,4,7,9-tetramethyl-5-decyn-4,7-diol(TM-diol), blends of 2,4,7,9-tetramethyl-5-decyn-4,7-diol(TM-diol), molecules having one or more acetylenic diol groups, cetyl alcohol, or any combination of any of these. In some embodiments, water-miscible solvents comprising food or USP grade oils, such as DMSO, DMF, castor oil, or any combination thereof, may be used. In one embodiment, a hydrophobic surfactant can be 2,4,7,9-tetramethyl-5-decyn-4,7-diol (TM-diol) or preparations thereof, such as SE-30 (Air Products), used in a concentration of up to about 0.5% by weight of surfactant micelle volume, and a water-miscible solvent can be DMSO. The concentration of surfactant selected should be sufficient to prepare an optically clear nanoemulsion, but not so much as to induce aggregation, since aggregation can lead to overly large nanoparticles.

The micelles carrying the cargo moieties (i.e., the surfactant micelles) can be coated with tumor-targeting moieties (e.g., tenfibgen) by mixing one or more targeting moieties with an aqueous dilution of the nanoparticles. In some embodiments, targeting moieties can be mixed with nanoparticles in a ratio (by weight) of about 1:500 to about 1:0.1 of targeting moiety to bioactive agent, depending upon factors including the targeting moiety and the rate at which the nanoparticle is desired to dissolve or disassemble. In one embodiment, the weight ratio is about 1:90 (that is, $\frac{1}{90}^{th}$) of targeting moiety to bioactive agent. In one embodiment, the weight ratio is about 1:40 of targeting moiety to bioactive agent.

Nanoparticle ligands may be modified by processes designed to enhance final nanoparticle function. As a non-limiting example, coating ligands may be readily modified with pharmaceutically acceptable heavy metals by re-precipitating protein in saturated ammonium sulfate solutions prepared with known levels of heavy metals. Incubation of about a 0.1-1 mg/ml solution of protein ligand at a ratio of 1:1 with a saturated ammonium sulfate solution is most expeditiously executed for about 4-36 hours before recovering metal-modified coating ligand by centrifugation. Metal concentrations in the ultrapure ammonium sulfate may range from, for example, 1 part per thousand to 1 part per trillion. As a further non-limiting example, tenascin polypeptides may be precipitated from cell culture supernatants using metal-containing ammonium sulfate, such that metals known to promote oxidative stress are adsorbed onto coating ligands preceding nanoparticles preparation.

To stabilize the ligand-adsorbed nanoparticle, the aqueous suspension of nanoparticles coated with one or more ligands can be mixed into an aqueous solution of metal ions (i.e., a "stabilization solution") capable of precipitating, crystallizing, or iontophoretic exchange with the coated nanoparticles. Representative, non-limiting examples of solutes that can be used to form coated nanoparticles include ionic species derived from elements listed in the periodic table. Ions may be included in the aqueous stabilization composition in a range from about, for example, 0.1 part per trillion to about 1 Molar (M). An adequate amount of ion should be included, such that the coated nanoparticles are sufficiently contacted with ions, but not so much that aggregation occurs, which can lead to overly large nanoparticles.

In one embodiment, a stabilization (or crystallization or receiving) solution can comprise about 10 millimolar (mM) $Ca^{2+}$ and about 126 mM $Li^{+}$. If ultrapure reagents are used in the stabilization solution, very small amounts (e.g., less than about 1 mM) of ions such as Ba, Fe, Mg, Sr, Pb and Zn may be added to optimize stabilization of the coated nanoparticles. In one embodiment, when the nanoparticles are prepared with sterile water, 126 mM of $Li^{+}$ is pre-treated with 2.5 ppb of $CS^{+}$ for increased stability. In one embodiment, a stabilization solution includes 10 mM $Ca^{2+}$, 126 mM Li+ (pre-mixed with 2.5 ppb $Cs^{+}$), 0.042 mM $Ba^{2+}$ with 14 nM $Sr^{2+}$, 6.25 nM $Mg^{2+}$ (all ultrapure, all prepared as stock solutions with sterile water, except $Sr^{2+}$ and $Mg^{2+}$, which are prepared with laboratory grade water, all metals are used as chloride salts, total bath volume approximately 30 ml). Flexibility of the system is demonstrated by nanoparticles showing high levels of cellular uptake that have been synthesized at lithium levels about 10-fold lower than those described here (data not shown). The artisan will understand that a variety of counter-ions can be used with these metals in the stabilization solution, such as chloride, sulfate, and nitrate.

The term "ultrapure", as used in reference to salts and metals, refers to salts and metals that are about or greater than 99% pure or of the highest purity available. The artisan will understand that ultrapure salts and metals are generally commercially available, and that, if required, altering effects of variations in content of such ultrapure materials on nanoparticle formulation can be addressed without undue experimentation by, for example, adjusting the baseline levels of other salts and metals that were used in previous formulations. Reducing the level of barium in a formulation can, for example, offset increases in the levels of impurities in calcium chloride dihydrate, to maintain size, shape, and/or function of formulated nanoparticles. As used herein, "laboratory grade" salts and metals refers to salts and metals that are not ultrapure. In order to maintain consistency of nanoparticle size, shape, and/or function for a given line of formulation, it is recommended that use of laboratory grade salts and metals be minimized, such as less than 25%, 20%, 15%, 10%, or 5% of the total weight of salts and metals added to the final salt receiving solution.

In one embodiment, the Cesium (Cs)-pretreated lithium nanoparticles comprise a polymorphic form that is differentiated from nanoparticles not pre-treated with Cs. This differentiation is evidenced by, for example, the substantive differences in melting point and FTIR spectra between Cs and non-CS nanoparticles presented in Table 1, below. As used herein, the terms "polymorph" and "polymorphic form" refer to solid crystalline-ordered forms of a compound or complex.

One or more solid state forms of a compound of interest such as a nanoparticle may be generated by crystallization. One or more solid state forms may also be generated by cocrystallization of a chemical substance with different guest molecules (i.e., components that are not the principal component of the crystal lattice). One or more solid forms may also be generated by inclusion of an element or element-combination into a supramolecular assembly or addition of a new element or element-combination to generate a new supramolecular assembly.

Among the phenomena in crystallization are the processes of nucleation and growth. Crystal nucleation is the formation of an ordered solid phase from liquids, supersaturated solutions, saturated vapors, or amorphous phases. Growth is the enlargement of crystals caused by deposition of molecules upon an existing surface. Nucleation may be induced by the presence of "seed" crystals. Some solid particle is present to provide a catalytic effect and reduce the energy barrier to formation of a new phase. Crystals may originate, for example, on a minute trace of a foreign substance (e.g., either impurities or scratches on container walls) acting as a nucleation site. Nucleation may also be promoted by external or nonchemical means, such as stirring the crystallization environment, or by applying both an initiating surface, together with physical energy, such as could be observed by the process of atomizing ultra-small nanoscale micelles into a salt solution.

Practically, polymorphic and novel forms of a compound such as a nanoparticle are known in the pharmaceutical arts to affect, for example, the solubility, stability, flowability, fractability, and compressibility of the compound, (Knapman, K. 2000 *Modern Drug Discovery* 3: 53-58). Therefore, the discovery of either new polymorphs of a nanoparticle drug or highly-related structural forms can provide a variety of advantages.

Polymorphs can be detected, identified, classified, and characterized using well-known techniques, such as, but not limited to, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Fourier-transform infrared spectroscopy (FTIR), Raman spectroscopy, hot stage optical microscopy, scanning electron microscopy (SEM), transmission electron microscopy (TEM), electron crystallography and quantitative analysis, particle size analysis (PSA), surface area analysis, solubility, and rate of dissolution.

As used herein, in reference to the spectra or data originally generated in graphical form (e.g., XRPD, IR, FTIR, Raman and NMR spectra), and unless otherwise indicated, the term "peak" refers to a peak or other special feature that one skilled in the art would recognize as not attributable to background noise. Some limited variance in interpreting or reading peak positioning can occur due to machine and/or algorithm variability in peak detection.

While not wishing to be bound by theory, the material science data presented in Table 1, below, indicate the addition of trace amounts of cesium (in the form of the element combination, i.e., cesium-treated lithium) surprisingly induced significant changes in the melting point and FTIR spectra of the inventive nanoparticles as compared to non-cesium nanoparticles. Changes in melting point indicates a new polymorphic form that corresponds with changes in physical state. The data presented in Table 1 link the measured changes in melting point with increases in nanoparticle stability, as manifested by improved shipping performance and extended Burton-derived in vitro release times.

As discussed elsewhere herein, nanoparticles formulated with cesium-treated lithium formed suitable nanoparticles with respect to size and shape (sub-50 nm spheroid, cuboid, or elliptical), while nanoparticles formulated with cesium simply commingled with lithium in the salt receiving bath did not. This supports the observation that it is the introduction of the element combination, i.e., cesium-treated lithium, and not simply the addition of cesium, which induced the significant changes in melting point and concomitant improved stability described above.

In one embodiment, the Cs-pretreated lithium sub-50 nanometer nanoparticles with a hydrophobic micelle core, ligand shell and an encapsulated bioactive agent comprise a novel polymorphic form of a supramolecular assembly (referred to herein as a Cs polymorph nanoparticle) of apparent molecular weight greater than 10,000 daltons, greater than 20,000 daltons, or greater than 30,000 daltons. The artisan can determine apparent molecular weight by standard methods such as for example, ultra high resolution aqueous size exclusion chromatography, using, for example, a Yarra 3u SEC-2000, 30 cm×7.8 mm column and UV detection together with a mobile phase of 0.3M NaCl in 0.1M phosphate buffer, pH 7.

In one embodiment, the element combination of cesium and lithium yields Cs polymorph nanoparticles that are/can be formed, used, and/or stored in an aqueous environment.

In another embodiment, the ligand shell of the Cs polymorph nanoparticle comprises tenfibgen. In still another embodiment, the ligand shell of the Cs polymorph nanoparticle comprises hyaluronan.

Nanoparticles that have a low surface charge, preferably as close to neutral as possible or even slightly negative, and/or that have the morphology of a compact or roughly spheroidal, cuboid, or elliptical shape, exemplify optimized stability. Additionally, any other components that are capable of increasing the stability of the nanoparticles can be included as part of the stabilization solution, such that the final mean diameter of the nanoparticles is between a range of about, for example, 5-50 nm. In certain embodiments, nanoparticles of a composition according to the invention have an average diameter of between about 5 and about 50 nanometers, between about 5 and about 40 nanometers, between about 5 and about 30 nanometers, or between about 5 and about 20 nanometers.

Particle size can be manipulated through routine variation of parameters, including, for example, the length of incubation time after crystallization in the salt receiving solution. In one embodiment, the nanoparticles are measured by atomic force microscopy (AFM). In another embodiment, the nanoparticles are measured by transmission electron microscopy (TEM). In another embodiment, the nanoparticles are measured by dynamic light scattering (DLS). In another embodiment, the nanoparticles are measured by size exclusion chromatography (SEC). In another embodiment, the nanoparticles are measured in dry state by methods known in the art. Unless otherwise stated, average diameter is expressed herein as the average of the major and minor axes of the nanoparticles as measured in dry state. Generally, formulations or compositions of nanoparticles with average major-to-minor-dimension ratios of greater than about 10:1, about 5:1, or about 3:1 are not suitable for uses intended herein.

For a more consistent size of nanoparticles, the nanoparticles can optionally be atomized into a receiving solution through a nozzle. Atomization should be sufficient to apply a shear force capable of breaking up flocculated aggregates without so much force as to induce hard aggregates. Those skilled in the art will understand that a particular nozzle diameter will lead to range of feed pressures suitable for atomizing the nanoparticles to a suitable and consistent size. In one embodiment, a nozzle diameter of about 250 microns or smaller with feed pressure of less than about 10 psi produces suitable nanoparticles.

The stabilized nanoparticles can be incubated at varying times and temperatures depending upon the amount of time required or desired for particle dissolution or disassembly in end use. Incubation times can vary from about 8 hours to about 7 days. In some embodiments, nanoparticles are incubated in round bottom tubes with nominal rotation at 4° C. for between 36 and 48 hours. Without wishing to be bound by theory, longer incubation times result in higher crystallization that increases both size and stability of the particle. After atomizing and/or incubating the nanoparticles in a stabilization solution, the nanoparticles can be filtered, centrifuged and/or dried to obtain a composition comprising separate and discrete sub-50 nm nanoparticles. In one embodiment, nanoparticles are centrifuged at 20,000×g at 4° C. for 2 hours and sterile-filtered through a 0.2 μm filter. The resultant nanoparticles can be frozen at about −20° C. or dried and reconstituted for later use. Sequences manufactured as chimeric polynucleotides are optionally propyl 3' end-blocked.

In one embodiment, the nanoparticles are prepared without polyethylene glycol (PEG) and similar species typically used to stabilize nanoparticles. In another embodiment, nanoparticles can be lyophilized and resuspended at lower, same, or higher concentrations, using standard methods known in the art.

Although the invention has been particularly shown and described with reference to a number of embodiments, it is understood by those skilled in the art that changes in the form and details may be made to the various embodiments disclosed herein without departing from the spirit and scope of the invention, and that the various embodiments disclosed herein are not intended to limit the scope of the claims.

The invention will be further described in the following examples, which likewise are not intended to limit the scope of the invention described in the claims.

EXAMPLES

Example 1—Formulation of Targeted Therapeutic Nanoparticles

Illustrative nanoparticles comprising diverse cargoes and targeting moieties were generated as follows.

Formula A:

In a 2 mL conical tube, 500 µg of chimeric oligo (SEQ ID NO: 5) polynucleotide against CK2 (phosphodiester 3' and propylendblocked—2'-OMe RNA chimeric, "LCK-6", (U.S. Pat. No. 7,741,304, incorporated herein in its entirety by reference)) in sterile water (HPLC grade, Fisher) at a concentration of 1 mg/ml was briefly vortexed, then complexed with 200 µg of 10 kD polyornithine (Sigma), and dispersed into 150 µl of sterile water using a water-insoluble surfactant system (TM-diol blend (SE-30, Air Product), 10 µg in 10 µg DMSO. Following emulsification with a water-miscible solvent (DMSO), by adding 150 µl of DMSO, vortexing, and subsequently placing in bath sonicator for 5 minutes, the complexes were then inverted and diluted by the addition of 700 µl of PBS.

The resultant hydrophobic micelles were coated (non-covalently) by the addition of 5.5 µg of recombinant fibrinogen fragment of tenascin (TBG), prepared by the method of Aukhill, et al. (*J. Biol Chem.*, 268:2542-53 (1993)), with modifications as described herein, placed in a bath sonicator for 15 minutes, transferred to a 5 ml polypropylene tube, and diluted up to 3 ml with PBS, then atomized with a manual actuator using an approximately 250 µm diameter orifice with feed pressure of less than about 10 psi into a salt receiving solution of sterile water containing primarily $Li^+$ (126 mM $Li^+$ (premixed with 2.5 ppb $Cs^+$ on $Li^+$), 10 mM $Ca^{2+}$, 0.042 mM $Ba^{2+}$ with 14 nM $Sr^{2+}$, 6.25 nM $Mg^{2+}$ (all ultrapure, all prepared as stock solutions with sterile water except $Sr^{2+}$ and $Mg^{2+}$ prepared with laboratory grade water, all metals were used as chloride salts, total bath volume approximately 30 ml). The total reaction volume was 36 ml. The level of the following metals tested for in the sterile water used to prepare the stabilization solution was determined to be less than 0.1 parts per million in sum total: aluminum, arsenic, barium, cadmium, chromium, copper, iron, lead, manganese, nickel, rubinium, sulfur, vanadium, and zinc.

The premixing step comprised adding $Cs^+$ at about 0.1 µg/1 ml to about 4M $Li^+$, at about 2.5 ppm $Cs^+$ to $Li^+$ by weight, in sterile water in a 50 ml tube, and rotating for about 2 minutes. Following cold-room incubation (4° C.) with nominal rotation in 40 ml round-bottomed tubes for 48 hours, which further stabilized the coated micelles in the salt solution, the sub-50 nm nanoparticles were recovered by centrifugation at 20,000×g at 4° C. for 2 hrs and resuspended in PBS+10% lactitol (at a concentration of 1 µg/µl), transferred to a 2 ml conical, and spun down at maximum speed for 5 minutes at 4° C., washed by resuspending pellet in PBS/10% lactitol, sterilized through a 0.2 µm filter, and frozen at −20° C.

In all formulations described in the instant example, a small amount (1% of coating weight) of Syrian Hamster IgG was "spiked" into the ligand coat to enable immunodetection of nanoparticle uptake by anti-Syrian Hamster antibodies. Average particle size was less than 50 nm, as measured by tapping mode atomic force microscopy using elliptical diameters of a 1 $e^{(-27)}$ g/ml sample dried down on a mica sheet. Average particle size is stated as the average of the major and minor axes of the measured nanoparticles. AFM measurements were further supported by TEM negative staining, where 1 ng/ml suspensions were spotted onto carbon grids. NIH Image J is used to calculate mean particle diameters. Most typically, the average particle size ranged from about 8 nanometers to about 30 nanometers. Formula A had an average particle diameter of 16±2.3 nm by TEM with a surface charge of −2.4±2.3 mev, as measured by a Zetasizer 4 dynamic light scattering device at a potential of 20 volts with a 2-minute pause between measurements in 1 mM KCl at 2 µg/ml.

Tenascin-Based Ligands:

Tenascin has been implicated in cancer activities and also as being specific for smooth muscle cells; furthermore, peptidic domains of tenascin have been identified, e.g., as in U.S. Pat. No. 6,124,260, and are known in the art. In one embodiment, tenascin suitable for the present invention is *H. sapiens* tenascin C, Genbank Accession No. NM_002160. Moreover, tenascin peptides and domains for adhesion with particular cell types, as well as functional and structural aspects of tenascin, have been disclosed and are known in the art, e.g., Aukhill, et al. 1993 *J Biol Chem* 268:2542-2553. Tenascin and/or any of its domains are suitable as ligands for the present invention. In one embodiment, the fibrinogen fragment of tenascin (also referred to herein as Fbg-L domain of tenascin-C or tenfibgen or TBG; nucleotide sequence of tenfibgen used in one embodiment of this invention as follows

```
                                            (SEQ ID NO: 10)
(atgattggactcctgtaccccttccccaaggactgctcccaagcaatg ctgaatggagacacgacctctggcctctacaccatttatctgaatggtg ataaggctcaggcgctggaagtcttctgtgacatgacctctgatggggg tggatggattgtgttcctgagacgcaaaaacggacgcgagaacttctac caaaactggaaggcatatgctgctggatttggggaccgcagagaagaat tctggcttgggctggacaacctgaacaaaatcacagcccaggggcagta cgagctccgggtggacctgcgggaccatggggagacagcctttgctgtc tatgacaagttcagcgtgggagatgccaagactcgctacaagctgaagg tggaggggtacagtgggacagcaggtgactccatggcctaccacaatgg cagatccttctccacctttgacaaggacacagattcagccatcaccaac tgtgctctgtcctacaaaggggctttctggtacaggaactgtcaccgtg tcaacctgatggggagatatggggacaataaccacagtcagggcgttaa ctggttccactggaagggccacgaacactcaatccagtttgctgagatg aagctgagaccaagcaacttcagaaatcttgaaggcaggcgtaagcggg cataa)
``` is used as the ligand. Tenascin, its subdomains, or any other biocompatible polymer ligand may be expressed or produced by methods known in the art or methods which the artisan can readily adapt. For illustration purposes, a method for producing TBG is provided below.

Tenfibgen (TBG) Preparation:

For all TBG formulas, unless otherwise noted, TBG was prepared by the method of Aukhil (*J Biol Chem* (268): 2542-2553 (1993)) with modifications, i.e. TBG was isolated and refolded from bacterial lysate by washing the insoluble pellet once with lysis buffer (50 mM Tris-HCl, 1.0 mM EDTA, 0.1 M NaCl, 0.2 mg/ml lysozyme, 0.1% Triton X-100, 0.1 mM PMSF, pH 8.0) containing 2 M urea and resuspending in 4M GuCL, 5 mM DTT in 0.02 M Tris-HCl, pH 8.0. After additional centrifugation, the clarified TBG solution was diluted with 2 M Guanidine-HCl, 20 mM Tris-HCl, pH 8.0 to make a final OD280 of about 1 and diluted dropwise about 10-fold into N2-sparged, 20 mM Tris-HCl, 0.2 M NaCl, 0.5 M Arginine-HCl for overnight stirred incubation (4° C.). After diafiltration against 20 mM Tris-HCl, pH 8.0 with an approximate 4-5 fold reduction in concentration and 0.45 μM filtration, a final purification was performed on heparan sepharose in 20 mM Tris-HCl, pH 8.0, with elution by bringing the NaCl concentration to 0.6 M. Endotoxin was removed in an anion exchange chromatography step by applying pH 10.5 Tenfibgen to Q Fast Flow resin, equilibrated with 20 mM $NaH_2CO_3$, 0.2M NaCl, pH=10.5, then readjusting pH to 7 with $H_3PO_4$ before final 0.2 um filtration. In therapeutic tumor-targeting formulations, TBG was reprecipitated in ultra-pure 40% ammonium sulfate containing 250 ppb $As^{+3}$, 25 ppm $Se^{+4}$, 2.5 ppm $Hg^{+2}$ and 25 ppm $Mo^{+5}$ for about 16 hours.

Formula B:

sub-50 nm nanoparticles coated with TBG were generated as described in Formula A, except that 6.3 mcg of TBG was added to 500 mcg of 2R-modified chimeric oligo (SEQ ID NO: 8), condensed with 125 mcg of 10 kD polyornithine (Sigma). When generating these nanoparticles, the TBG-coated micelles were atomized into the salt receiving solution of Formula A except for the following modified concentrations: 4.5 nM $Sr^{2+}$, 2.25 nM $Mg^{2+}$. Average particle diameter was less than 50 nm (17.8±3.1 nm), as measured by negative staining TEM using elliptical diameters of a 1 ng/ml sample spotted onto a carbon grid, with a surface charge of −7.7±4.2 mev, as measured by a Zetasizer 4 dynamic light scattering device at a potential of 20 volts with a 2-minute pause between measurements in 1 mM KCl at 2 μg/ml.

Formula C:

sub-50 nm nanoparticles coated with TBG were generated as described in Formula A, except that 2.6 mcg of TBG was added to 250 mcg of chimeric oligos (SEQ ID NOs:5 and 6, 1:1 by weight) condensed with 100 mcg of 10 kD polyornithine (Sigma) and micellized using 7.5 ug surfactant. When generating these nanoparticles, the TBG-coated micelles were atomized into the salt receiving solution of Formula A modified for the following concentrations: 3.75 nM $Sr^{2+}$, 4.68 nM $Mg^{2+}$. Average particle diameter was less than 50 nm (17.8±1.5 nm), as measured by negative staining TEM using elliptical diameters of a 1 ng/ml sample spotted onto a carbon grid, with a surface charge of −12.3±3.5 mev, as measured by a Zetasizer 4 dynamic light scattering device at a potential of 20 volts with a 2-minute pause between measurements in 1 mM KCl at 2 μg/ml.

Formula D:

sub-50 nm nanoparticles coated with TBG were generated as described in Formula C, except the oligonucleotide mix consisted of SEQ ID NOs: 5 and 7 (1:1 by weight). Average particle diameter was less than 50 nm (17±1.6 nm), as measured by negative staining TEM using elliptical diameters of a 1 ng/ml sample spotted onto a carbon grid, with a surface charge of −7.1±5.4 mev, as measured by a Zetasizer 4 dynamic light scattering device at a potential of 20 volts with a 2-minute pause between measurements in 1 mM KCl at 2 μg/ml.

Formula E:

sub-50 nm nanoparticles coated with TBG were generated as described in Formula A, except that 3.1 mcg of TBG was added to 250 mcg of 2R-modified chimeric oligos (SEQ ID NOs: 8 and 9, 1:1 by weight) condensed with 62.5 mcg of 10 kD polyornithine (Sigma) and micellized using 7.5 ug TM-diol. When generating these nanoparticles, the TBG-coated micelles were atomized into the salt receiving solution of Formula A modified for the following concentrations: 2.5 nM $Sr^{2+}$, 0.25 nM $Mg^{2+}$. Average particle diameter was less than 50 nm (19.5±1.5 nm), as measured by negative staining TEM using elliptical diameters of a 1 ng/ml sample spotted onto a carbon grid, with a surface charge of −5.8±3.9 mev, as measured by a Zetasizer 4 dynamic light scattering device at a potential of 20 volts with a 2-minute pause between measurements in 1 mM KCl at 2 μg/ml. Lithium content was assessed as 5.39 ng of $Li^+$ per μg of oligo by ICP-AES. (It is noted that for an analogous formulation, lithium content of 292 pg/ug of oligo was measured by the more sensitive ICP-MS method.)

Formula F:

sub-50 nm control nanoparticles coated with TBG were generated as described in Formula A, except that 6.3 mcg of TBG was added to 500 mcg of a 2R-modified chimeric oligo (anti-coagulation Factor VII, as reported in Akinc, et al. 2008 *Nat Biotechnol* 26:5(561-9)) condensed with 125 mcg of 10 kD polyornithine (Sigma) and micellized using 5 ug TM-diol. When generating these nanoparticles, the TBG-coated micelles were atomized into the salt receiving solution of Formula A modified for the following concentrations: 1.17 nM Sr2+, 4.68 nM Mg2+. Average particle diameter was less than 50 nm (24.7±3 nm), as measured by negative staining TEM using elliptical diameters of a 1 ng/ml sample spotted onto a carbon grid, with a surface charge of −7.6±2.4 mev, as measured by a Zetasizer 4 dynamic light scattering device at a potential of 20 volts with a 2-minute pause between measurements in 1 mM KCl at 2 μg/ml.

Formula G:

sub-50 nm nanoparticles coated with TBG were generated as described in Formula A, except that the stabilization solution was comprised of non-sterile, laboratory-grade water, and the Lithium Chloride stock was not pretreated with cesium or any other ion. The level of the following metals tested for in the water used to prepare the stabilization solution was determined to be about 0.9 parts per million in sum total: aluminum, arsenic, barium, cadmium, chromium, copper, iron, lead, manganese, nickel, rubinium, sulfur, vanadium, and zinc. Nanoparticles were resuspended following centrifugation in PBS+10% Lactitol. Average particle diameter was less than 50 nm (21.8±4 nm), as measured by negative staining TEM using elliptical diameters of a 1 ng/ml sample spotted onto a carbon grid, with a surface charge of −9.6±3.8 mev, as measured by a Zetasizer 4 dynamic light scattering device at a potential of 20 volts with a 2-minute pause between measurements in 1 mM KCl at 2 μg/ml.

Formula H:

sub-50 nm nanoparticles coated with TBG were generated as described in Formula A using the same LCK oligo. When generating these nanoparticles, the TBG-coated micelles were atomized into the salt receiving solution of Formula A based on Lithium Nitrate, rather than Lithium Chloride and modified for the following concentrations: 7.5 nM $Sr^{2+}$, 5.0 nM $Mg^{2+}$. Average particle diameter was less than 50 nm (21.5±2 nm), as measured by negative staining TEM using elliptical diameters of a 1 ng/ml sample spotted onto a carbon grid with a surface charge of −12.4±4 mev, as measured by a Zetasizer 4 dynamic light scattering device at a potential of 20 volts with a 2-minute pause between measurements in 1 mM KCl at 2 µg/ml.

Formula I:

sub-50 nm nanoparticles coated with 20 kD MW hyaluronan (Sodium Hyaluronate powder resuspended in HPLC water, Lifecore Biomedical, Lha, low molecular-weight hyaluronan) were generated as described in Formula G, except that 3.1 mcg of HA (substituted for TBG) was added to 125 mcg of plasmid DNA (pVivoβgal, Invivogen Corp., 10.5 kb) (substituted for oligonucleotides), first complexed with 19.4 µg of 25 kDa polyethyleneimine (PEI; Sigma Chemical Co., St. Louis, Mo.), a branched cationic polymer, then micellized with 6.25 ug of TM-diol. When generating these nanoparticles, the Lha-coated micelles were atomized into the salt receiving solution of Formula G modified for the following concentrations and additions: 2 nM $Sr^{2+}$, 0.5 nM $Mg^{2+}$, 0.54 $Bi^{2+}$ µM, and addition of 0.40 mM $Ni^{2+}$ (ultrapure, basis of 40 ml total volume). Average particle diameter was less than 50 nm (20.4±2), as measured by negative staining TEM using elliptical diameters of a 1 ng/ml sample spotted onto a carbon grid with an average surface charge of −8.1±4.7 mev, as measured by a Zetasizer 4 dynamic light scattering device at a potential of 20 volts with a 2-minute pause between measurements in 1 mM KCl at 2 µg/ml.

Formula J:

sub-50 nm nanoparticles coated with 20 kD MW hyaluronan (Sodium Hyaluronate powder resuspended in HPLC water, Lifecore Biomedical, Lha, low molecular-weight hyaluronan) were generated as described in Formula A, except that 3.1 mcg of HA (substituted for TBG) was added to 125 mcg of plasmid DNA (pVivoβgal, Invivogen Corp., 10.5 kb) (substituted for oligonucleotides), first complexed with 19.4 µg of 25 kDa polyethyleneimine (PEI; Sigma Chemical Co., St. Louis, Mo.), a branched cationic polymer, then micellized with 6.25 µg of TM-diol. When generating these nanoparticles, the Lha-coated micelles were atomized into the salt receiving solution of Formula A modified for the following concentrations and additions: 2 nM $Sr^{2+}$, 0.5 nM $Mg^{2+}$, 0.54 $Bi^{2+}$ uM and addition of 0.40 mM $Ni^{2+}$ (ultrapure, basis of 40 ml total volume). Average particle diameter was less than 50 nm (22.7±5 nm), as measured by negative staining TEM using elliptical diameters of a 1 ng/ml sample spotted onto a carbon grid with an average surface charge of −6.4±4.2 mev, as measured by a Zetasizer 4 dynamic light scattering device at a potential of 20 volts with a 2-minute pause between measurements in 1 mM KCl at 2 µg/ml. $Li^+$ content of between 8.1-13.1 ng/µg of plasmid have been measured in similar formulations by ICP (data not shown). By routine characterization and TEM, plasmid s50 particles of Formula I and J were found to be similar to TBG-coated oligo particles of Formulas A-H in terms of physical properties and comparable TEM. For example, regardless of nucleic acid cargo, nanoparticle encapsulation yields for the formulas described herein were greater than 95%, as determined by the modified method of Burton (Kren, et al. 2009 JCI 119:2086-99) (data not shown). This similarity of properties between the nanoparticles comprising an oligonucleotide bioactive agent and protein shell and the nanoparticles comprising a plasmid DNA bioactive agent and carbohydrate shell demonstrates the flexibility of the nanoparticle formulation process and resulting nanoparticle composition to accommodate different bioactive agents, polymers, and ligand moieties.

Example 2—Cesium Modification of the Lithium Ion in Nanoparticle Synthesis Improves Stability Besides being efficacious, nanoparticle dosage forms must comply with the requirements of pharmaceutical manufacturing and product requirements from regulatory and other entities. For example, a nanoparticle's physical stability is a key component of its regulatory approval, impacting formulation, manufacturing, and storage protocols. Trace addition of cesium to the nanoparticle synthesis when executed in sterile water, has been found, surprisingly, to result in improved physical stability, as manifested by enhanced shipping performance and Burton-derived stability measures.

It has been discovered, quite unexpectedly, that 2.5 ppb cesium pre-treatment of the lithium before assembling the receiving solution into which the ligand-stabilized micelles are added quadruples the concentration at which nanoparticles bearing either oligonucleotides or plasmid DNA may be shipped as liquid formulations by air freight at −4° C. These observations are summarized in Table 1. In these air shipping tests, nanoparticle suspensions were concentrated by lyophilization, shipped, and subsequently examined upon return for changes in particle diameter by TEM microscopy following an air shipping challenge. In TEM, the inventive nanoparticles appear as cubic or fractal supramolecular assemblies surrounded in a visible, but poorly refractive corona, comprised of targeting ligand (data not shown). For example, suspension concentrations of 20 mg/ml are required to acquire light scattering data for (i.e., to detect) the nanoparticles (sized approximately 25 nanometers in diameter) in low power (1 mW) dynamic light scattering (DLS). In contrast, ligand-coated micelles preceding incubation in the cesium-treated lithium salt receiving solution, while similarly small in size (28 nm diameter, Table 1), are readily detected at concentrations of about 1 mg/ml under similar DLS conditions, suggesting significant change in nanoparticle supramolecular assembly occurs during the incubation/stabilization step (data not shown).

In shipping and control samples, particle diameters were quantified by image analysis in NIH Image J as the average of elliptical axes fitted to particles from TEM micrographs. Results are summarized in Table 1 to show that for a non-modified cesium formulation bearing oligo (Formula G), average particle diameter increased 161% from a control formulation to the same formulation air-shipped at 3 mg/ml. A concomitant loss in protein corona surrounding the faceted, birefringent particle was also observed after shipping (data not shown). In contrast, the analogous cesium-modified formulation (Formula A) maintained shape and corona at 4 mg/ml (Table 1, data not shown).

The same analysis was executed for a pair of formulations bearing a commercial reporter gene plasmid and coated with hyaluronan with a similar result. For Formula J, prepared with cesium pre-treatment of the lithium in the receiving bath, particles could be shipped at an 8-fold increase in concentration (2 vs. 0.25 mg/ml) with less than 15% increase in particle diameter relative to Formula I, prepared without cesium pretreatment. A loss in ligand corona was also observed in the non-cesium pretreated particles with increased shipping concentration also (data not shown). The improvement in shipping concentration demonstrated with Formula H, prepared with Lithium Nitrate rather than Lithium Chloride, indicates that multiple salts of lithium may be used in nanoparticle synthesis. While premixing of cesium and lithium prior to their addition to the salt receiving solution resulted in nanoparticles of suitable spherical or cuboid ultra-small (LTE 50 nm dry diameter) morphology, the unmixed addition of cesium and lithium to the salt receiving solution did not (data not shown).

ton assay (Kren, et al. 2009 *JCI* 119:2086-99). In this assay, particles are incubated at 56° C. in 1M NaOH overnight rather than 6M NaOH. The nanoparticles were then neutralized and the Burton reagents added to create a blue signal upon reaction with released DNA. Percent yield is expressed relative to a theoretical value from a standard curve, so that 100% yield is approached as the nanoparticles are fully degraded to release their contents. In vitro release is then expressed as an endpoint interpolated from timepoints sur-

TABLE 1

Particle and shipping stability with + without cesium modification

| Particle/Cargo | Formula | Particle Diameter[1] (nm) | % Δ from control | In vitro release[2] Hrs | % Δ | DSC Transitions[3], ° C., gt midpoints, et nadirs | FTIR spectrum[7] (wavenumber, cm −1) |
|---|---|---|---|---|---|---|---|
| PBS + 10% Lactitol | | | | | | gt 160; sharp et, 186 | |
| TM-Diol surfactant[4] | | | | | | | quad, 2956, 2928, 2873, 2832; singlet, 1733; triplet, 1449, 1370, 1260; group of 5; singlet, 805 |
| Ligand-coated micelle[4] | | 28.2 ± 1.6 | | | | broad et, 98, 105 (45-126) | |
| TBG LCK oligo (− Cs) | G | 21.8 ± 0.9 | — | 62 | — | gt 158; strong, broad et, 180 (172-200) | v brd, 3329; quad, 2952, 2921, 2873, 2839; s brd singlet, 1647; md triplet, 1456, 1377, 1260; v st doublet, 1079, 1031; md singlet, 798 |
| 1 mg/ml shipped | | 27.4 ± 1.4 | +26* | | | | |
| 2 mg/ml shipped | | 35.9 ± 1.2 | +65* | | | | |
| 3 mg/ml shipped | | 57 ± 3.4 | +161* | | | | |
| TBG LCK oligo (+ Cs) | A | 24.8 ± 2.5 | | 104 | +68 | et, 130, 137, 275 | v brd, 3377; triplet, 2952, 2925, 2853; doublet, 1740, 1644; md triplet, 1462, 1377, 1260; v st doublet, 1093, 1021; md singlet, 795 |
| 2 mg/ml shipped | | 24.7 ± 1.8 | 0 | | | | |
| 3 mg/ml shipped | | 25.7 ± 1 | +4 | | | | |
| 4 mg/ml shipped | | 21.4 ± 1.1 | −14 | | | | |
| TBG LCK oligo(+ Cs) | H | 21.5 ± 0.5 | | 82 | +33 | | |
| 3 mg/ml shipped | | 22.8 ± 0.9 | +6 | | | | |
| LhaNi pVivoβgal (− Cs) | I | 20.4 ± 0.5 | — | 117 | — | gt 158; strong, broad et, 178(172-227)[5] | |
| 0.25 mg/ml, shipped | | 23.4 ± 0.9 | +15 | | | | |
| 0.5 mg/ml, shipped | | 32.3 ± 1.3 | +58* | | | | |
| 1 mg/ml, shipped | | 34.4 ± 2.2 | +69* | | | | |
| 2 mg/ml, shipped | | 36 ± 1.6 | +76* | | | | |
| LhaNi pVivoβgal (+ Cs) | J | 22.7 ± 1.1 | | >120[6] | +++ | vs gt 150; sharp et, 193, 206, 227° C.[5] | |
| 0.25 mg/ml, shipped | | 21.6 ± 0.7 | −5 | | | | |
| 0.5 mg/ml, shipped | | 21 ± 0.9 | −7 | | | | |
| 1 mg/ml, shipped | | 23.8 ± 1.3 | +5 | | | | |
| 2 mg/ml, shipped | | 25.5 ± 1.6 | +12 | | | | |

Notes:
*= $p < 0.5$,
[1] Particle diameter was measured as average elliptical diameter after drying at 0.1 ng/ml by negative staining TEM at x271,000. Expressed as mean ± SE with 15-20 measurements per analysis. Lots were confirmed to have substantial in vitro cellular uptake into tumor cells grown in 3-D culture before use in shipping studies.
[2] In vitro release was measured in conjunction with DNA incorporation by a colorimetric, modified Burton assay employing a standard curve. Release is reported as a timepoint interpolated from later time points with average Burton yields surrounding 100%.
[3] Thermal transitions were identified from thermograms generated by differential scanning calorimetry (DSC). Suspensions were dried to produce powder for analysis, and 1-2 mg were scanned at 20° C./min from room temperature to about 400° C. in crimped aluminum pans. abbreviations, gt, glass transition; et, endotherm; vs, very small.
[4] TM-Diol is unformulated hydrophobic surfactant and is presented for analysis reference. Ligand-coated micelles are micelles formulated according to Formula E but were scanned prior to incubation in salt receiving solution.
[5] Hyaluronan-coated ligand particles were similar formulations to shipping samples but comprised 8.5 kb reporter gene plasmids rather than 10.5 kb reporter plasmids.
[6] After about 120 hours in this form of assay, color started to degrade in the standard curve, necessitating, here, the premature termination of the assay.
[7] The FTIR spectra were recorded using a Perkin Elmer Spectrum 65, equipped with a ATR attachment, a mid- infrared source as the excitation source, and a DTGS detector. The spectra were acquired in 32 scans at resolution of 4 cm$^{-1}$. Suspension samples were extracted with 3:1 (v/v) of isobutyl to isoamyl alcohol at 4° C. to remove residual surfactant and evaporated, dried powder was submitted for analysis. Abbreviations, v, very; s, small; md, moderate; str, strong; brd, broad.

The impact of cesium pre-treatment of lithium preceding assembly of the receiving solution on particle stability was further investigated by examining formulations for in vitro release. In vitro release was assessed in conjunction with particle degradation based on a modified colorimetric Burton assay. Thus, in vitro release time is a measure of the nanoparticle's resistance to degradation, and its increase following Cs-pre-treatment corresponds with the increase in shipping stability observed for Cs-treated vs. non-CS-treated nanoparticles for both oligo and plasmid series (Table 1 in vitro release times; Cs vs. non-Cs oligo, 104 hrs. vs. 62 hrs.; Cs vs. non-Cs plasmid DNA, >120 hrs. vs. 117 hrs.).

To investigate how differences in nanoparticle composition might impact the inventive nanoparticles at a physical (release) and functional (shipping) level, thermal profiles of the dried and crushed powder of the oligo and plasmid-bearing nanoparticles were examined for potential changes in characteristic transitions by differential scanning calorimetry at 10° C. per minute over a range from about 25° C. to about 400° C. (summarized in Table 1, above). In multiple runs, a small transition at 158° C., followed by a strong, broad endotherm (172-200° C.) with nadir at 180° C., was observed in the non-Cs-modified Formula G, while only one strong endotherm at 275° C. was observed for Cs-modified Formula A, indicating a change in morphological state. Similarly, for hyaluronan nanoparticles bearing 8.5 kb reporter gene plasmids, in the non-Cs-modified compound (representing Formula I), a small transition at 158° C. followed by a strong and broad endotherm with nadir at 178° C. (172-227) was observed, compared to the Cs-modified compound, where a very small transition at 150° C., with strong, very sharp endotherms at 193, 206, and 227° C., was observed (representing Formula J), again indicating a change in morphological state. In contrast, a scan of the diluent, PBS+10% lactitol, a non-reducing sugar, showed a very small transition at about 160° C. and a strong, sharp endotherm at 186° C. with a degradation endotherm centered around at about 310° C. All nanoparticle compounds showed such an endotherm centered around 307-313° C. A thermal scan of a TBG-coated micelle before atomization and subsequent incubation in the primarily lithium salt solution ("Ligand-coated micelle") showed a broad endotherm with peaks (98, 105° C.) centered around 100° C. The observation that this thermogram was markedly different from the nanoparticles scanned post incubation in the cesium-treated lithium solution supports the statement that the cesium-treated lithium solution imparts order and rearrangement to the stabilized micelle and nanoparticle over time to create a unique supramolecular assembly.

Compound differences upon introducing cesium-pretreatment of lithium into the stabilization bath were further investigated by FTIR spectroscopy. The FTIR spectrum of non-Cs Formula G and Cs-containing Formula A were read from 600-4000 $cm^{-1}$. Based on peak assignment derived from component and library scans, the capsule scans were generally characterized by a broad, intensive band around 3300, representing the O—H stretching vibration of water at 3390 $cm^{-1}$, groups of bands attributable to the surfactant (4: at about 2956-2832 $cm^{-1}$, 3: at about 1449-1260 $cm^{-1}$) and a strong, intensive band attributable to Li—O and Li—O H vibrations at about 1100-1110 $cm^{-1}$. Major peak differences observed upon cesium-pretreatment of the stabilizing bath (Formula G vs. Formula A) were: 1) the narrowing of a broad peak at about 1647 $cm^{-1}$ into peaks at about 1740, 1640; 2) the modification of a likely surfactant-derived quadruplet at about 2952-2839 into a triplet at about 2952-2853; and 3) a shift in the water vibration band from about 3329 to 3377 $cm^{-1}$.

In terms of absorbance shifts, cesium pretreatment resulted in a greater than 50% decrease in the magnitude of the water absorbance, consistent with a possible decrease in the amount of water trapped within a reorganized capsule assembly. Of note, the hydrophobic surfactant was devoid of absorbances in this region. There were also greater than 50% absorbance increases in the surfactant-attributable bands at about 1260 and 795 $cm^{-1}$ nearest to the lithium region, suggesting possible changes in the interactions between these critical components of the assembly. Following atomization of the ligand-coated micelle into the receiving bath comprised of cesium-treated lithium, these components are in intimate contact for a number of hours before the reaction is stopped.

Significant changes in thermal transitions and IR spectra are important indicators of polymorphic change in crystalline compounds, pharmaceutical compounds, and nanoscale supramolecular assemblies, which are known to undergo, in different morphology states, important physical and functional change. Without wishing to be bound by theory, the indicated differences (Table 1) in morphological state for Cs-modified nanoparticles compared with unmodified nanoparticles potentially provides an important mechanism underlying the improved shipping stability and extended Burton-derived in vitro stability observed for the Cs-modified nanoparticles.

This example shows that the inventive nanoparticles substantially increase shipping concentrations and Burton-derived stability for diverse cargoes and nanoparticle polymorphs.

Example 3—Modified Chimeric Polynucleotide Mix Demonstrates Surprising Efficacy in a Mouse Tumor Model The cesium-modified nanoparticles comprising TBG ligands and anti-CK2 chimeric polynucleotide bioactive agents are directed toward manipulating levels of Casein Kinase 2alpha (Csnk2a1) and Casein Kinase 2alphaprime (Csnk2a2) protein in tumor and tumor stromal cells, as the TBG ligand in the nanoparticle delivery system directs particle and oligo cargo to both tissue types. Casein Kinase 2 (CK2) is a ubiquitous enzyme overdriven by tumor cells to promote survival by multiple pathways, and it accumulates in cell nuclei under conditions of stress and in tumors. Shuttling of CK2 from the nuclear compartment precedes apoptosis, and the inability of the tumor cell to maintain nuclear CK2 precedes tumor death. Oncology therapeutics are often evaluated in human tumors grown in immunocompromised mice (xenograft models). As outlined in Table 2, below, in the regions of the genes targeted with the bifunctional oligos engaging Ago2 and RNAseH (U.S. Patent Publication No. 2013/0267577, incorporated herein in its entirety by reference), up to 3 mismatches can exist between human and mouse (3 between hu Csnk2a1 and mu Csnk2a2). Mismatches to hu Csnk2a1 are highlighted by shading and either bolded underline, outlined, or oversize letters.

Upon incorporating a single-nucleotide modification into the single-strand oligo design described herein (SEQ ID NO: 8), as well as into a novel single-strand oligo design directed to Csnk2a2 (SEQ ID NO: 9), and combining these single-strand oligos in TBG-coated s50 particles to form a CK2 anticancer therapeutic mix, significant results in terms of inhibition of tumor growth, cell proliferation, and inflammation were achieved in tumor-bearing mice. The 2R backbone modification consisted of changing a single nucleotide—the DNA nucleotide at position 2 from the 5'-end to a 2'-O-methyl-modified RNA nucleotide. All backbone linkages in these oligos were phosphodiester. In this experiment, efforts were also made to assess the impact of mismatching analogous murine target regions. Table 2, below, describes the sequences used or referred to in the instant example:

TABLE 2

Sequences

| DNA | Target-perfect match | SEQ ID NO: | Sequence |
|---|---|---|---|
| Hu Sxnk2a1 | | 1 | ATGTGGAGTTTGGGTTGTAT |
| Hu Csnk2a2 | | 2 | ATGTGGAGTTTGGGCTGTAT |
| Mu Csnk2a1 | | 3 | ATGTGGAGCTTGGGTTGTAT |
| Mu Csnk2a2 | | 4 | ATGTGGAGCTTGGGCTGCAT |
| Oligos | | | |
| LCK | Hu Csnk2a1 | 5 | 5'ATACAACCCAAACT ccacau -propyl-3' |
| huCK2prime | Hu Csnk2a2 | 6 | 5'ATACAGCCCAAACT ccacau -propyl-3' |
| muCK2prime | Mu Csnk2a2 | 7 | 5'ATGCAGCCCAAGCT ccacau-propyl-3' |
| Modified Oligos | | | |
| 2RLCK | Hu Csnk2a1 | 8 | 5'AuACAACCCAAACT ccacau -propyl-3' |
| 2RhuCK2prime | Hu Csnk2a2 | 9 | 5'AuACAGCCCAAACT ccacau -propyl-3' |

Notes:
1) All nucleotide linkages are phosphodiester.
2) Italics in DNA target sequences = 2'O-Methyl RNA region in the 3' end of the corresponding chimeric drug oligo.
3) Mismatches to Hu Csnk2a1 are shaded and contain either shaded underline, boxed, or oversize underline letters.
4) For Oligos and Modified Oligos, caps denote DNA, lower case denotes RNA, and all RNA nucleotides are 2' O—Me modified.

Using two strains of nude mouse (FoxN, Balb/CaNCR (BN)) and one tumor line (FaDu, hypopharyngeal), mice were inoculated intradermally with either $2e^6$ (FoxN) or $2e^5$ (BN) tumor cells in 50% Matrigel, and subcutaneous treatment was initiated 7 days later. Average tumor size at start of treatment was approximately 69-86 cu mm. Cohorts of 5 mice were treated at 10 µg/kg twice weekly. In some cases, after approximately 10 days of treatment, 2 mice from a treatment group were sacrificed. After 30 days of treatment (D30), the remaining 3-5 animals per group were sacrificed, and residual viable tumors were weighed.

To assess molecular changes, cryosections from viable tumor regions from each mouse were assayed for Ki-67 and p65 NF-kB levels by microscopy and quantified as signal area fraction thresholded against background controls using NIH Image J. Duplicate representative fields were collected from viable tumor sections representing all D30 mice. Ki-67 is a common clinical indicator of tumor proliferation rate and is expressed as a fraction or percentage of viable cell nuclei area, and p65 NF-kB is a major signaling and regulatory protein in inflammation and is an important downstream target of CK2. NF-kB is aberrantly activated, and inhibition of NF-kB induces cell death and inhibits tumorigenesis in head and neck squamous cell carcinomas (HNSCC) (Yu, et al. 2006 Cancer Research 66:6722-6731). The artisan, thus, appreciates the potency and many of the results of anti-CK2 strategies in tumor models can be understood in terms of anti-NF-kB activity. In terms of cell biology, p65 NF-kB (similar to CK2) localizes to cell nuclei under inflammatory conditions and conditions of stress, and is cytoplasmic or less detectable with increasing reduction in inflammation. Table 3 summarizes treatments and results for the three analyses.

TABLE 3

Results 30 days after start of treatment in mouse Fadu tumor model

| Treatment | SEQ ID NO: | Formula No.[5] | Tumor Weight (g) | % Δ | Ki-67 Index (signal area/ nuclear area) | % Δ | NF-kB Index (signal/tissue area) | % Δ |
|---|---|---|---|---|---|---|---|---|
| Experiment E1-Effect of 2R modification on starting single-stranded oligo in FoxN mouse model. | | | | | | | | |
| Control | | | 1.03 ± 0.04 | | 0.8 ± 00.13 | | 0.87 ± 0.06 | |
| 2RLCK | 8 | B | 0.58 ± 0.19 | −43.7 | 0.87 ± 0.09 | +9 | 0.69 ± 0.06 | −20.4 |
| LCK | 5 | A | 1.043 ± 0.22 | 0 | 1.1 ± 0.32 | +44 | 0.8 ± 0.1 | −7.5 |
| Experiment E2-Effect of oligo mix perfect match approach without 2R modification in BN mouse model | | | | | | | | |
| Control | | | 0.634 ± 0.17 | | 0.96 ± 0.05 | | 0.78 ± 0.01 | |
| muMix | 5 + 7 | D | 0.8 ± 0.07 | +26.2 | 0.85 ± 0.33 | −11 | 0.31 ± 0.05 | −59.7* |
| huMix | 5 + 6 | C | 0.85 ± 0.06 | +34.1* | 0.89 ± 0.42 | −6.5 | 0.82 ± 0.12 | +5.1 |
| LCK | 5 | A | 1.0 ± 0.39 | +57.7 | 1 ± 0.16 | +5.5 | 0.74 ± 0.01 | −5.3 |

TABLE 3-continued

Results 30 days after start of treatment in mouse Fadu tumor model

| Treatment | SEQ ID NO: | Formula No.[5] | Tumor Weight (g) | % Δ | Ki-67 Index (signal area/ nuclear area) | % Δ | NF-kB Index (signal/tissue area) | % Δ |
|---|---|---|---|---|---|---|---|---|
| Experiment E3-Effect of combined 2R modification and oligo mix approach in BN mouse model | | | | | | | | |
| Control | | | 0.68 ± 0.24 | | 0.89 ± 0.11 | | 0.89 ± 0.09 | |
| 2R huMix | 8 + 9 | E | 0.29 ± 0.04 | −56.1*# | 0.24 ± 0.1 | −73* | 0.0029 ± 0.002 | −99.7* |

Notes:
[1] N = 3 mice per group, except for huMix which had 5.
[2] Values are reported as mean ± SE.
[3] * = p < 0.05, Student's t-test.
[4] # = p < 0.05, Student's t-test, significant against entire BN control pool, 0.66 ± 0.11 g.
[5] Formula number for TBG nanoencapsulated sequence as listed under and described in Example 1.

Of note, despite limited differences between the oligonucleotide components of the experiment groups, the TBG-encapsulated 2R huMix oligo was the only approach that produced significant reductions in all three categories of tumor weight, cell proliferation (Ki-67), and inflammation index (NF-kB) vs. controls 30 days after the start of treatment (Table 2, E3 experiment, Formula E). Neither the encapsulated single-nucleotide 2R modification (E1 experiment, Formula B) nor the encapsulated huMix approach (E2 experiment, Formula C) showed a significant decrease in tumor weight at 30 days post-treatment. Indeed, the huMix-treated group (Formula C) showed a significant increase of 34% in tumor weight relative to control. Conversely, the tumors from mice treated with nanoencapsulated 2RhuMix (Formula E) showed a significant 56% reduction in tumor weight against pooled BN control tumors that corresponded with large and dramatic reductions in cell proliferation and inflammatory index (−73% Ki-67 index, −99.7% p65 NF-kB signal fraction, p<0.05). No other treatment group showed significant reduction in both cell proliferation index and p65 NF-kB signal vs. controls, much less those two measures and tumor weight. The muMix treatment in the E2 experiment showed a significant 59.7% reduction in NF-kB signal area fraction vs. controls, but this was accompanied by a 26.2% increase in tumor weight vs. controls, a clearly undesired outcome. Of additional note, in the E3 experiment, there was significant reduction (99.7%) in p65 NF-kB signal in the 2R huMix cohort vs. controls, whereas there was little change in p65 NF-kB signal in the huMix cohort in the E2 experiment, where mismatches to murine sequences were equal to those of the 2R huMix (Table 2, above).

Changes in CK2 alpha and CK2 alpha prime protein levels for the mice in the E3 experiment were assessed by microscopy. Consistent with significant decreases in shrinkage, proliferation, and inflammation indices, significant reduction (p<0.05) in CK2 alpha and CK2 alpha prime signal levels (−52% and −45%, respectively) was observed in viable tumor sections of treated mice relative to controls (data not shown). No significant changes in CK2 alpha and CK2alpha prime signal fraction were observed in all other treatments in experiments E1 and E2.

It is noted that the treated mice in E3 experiment showed no significant weight loss or untoward effects during the 30-day observation period (data not shown). Taken together, the observed results show that the combination of limited modifications in oligonucleotide backbone and sequences resulted in significant and surprising changes in phenotypic and molecular markers in tumor-bearing mice.

Example 4—Modified Chimeric Polynucleotide Mix Demonstrates Surprising Efficacy in an Aggressive, Xenograft Mouse Tumor Model To investigate the effect of limited modifications in oligonucleotide backbone and sequences, together with Cs-modification of nanoparticle, in another model, a xenograft tumor model comprising the human tumor line (UM-SCC-47, derived from HPV-(+) tongue tissue) and NIH outbred athymic nude mice were examined. In this experiment, nude mice were inoculated subcutaneously with $2e^6$ cells and held for two weeks, while tumors grew to 60-80 cu. mm. before starting daily SQ treatment at 100 μg/kg. Tumors were collected after 14 days of treatment and examined similarly as in the FaDu experiment described above. Results are summarized below in Table 4.

In this example, similar to example 3 and using the same methods, the Cs-modified, TBG-encapsulated 2R huMix oligo produced the largest reductions in all three categories of tumor weight, cell proliferation (Ki-67), and inflammation index (p65 NF-kB) vs. controls at 14 days (rather than 30 days) after the start of treatment (Table 4, Formula E). Additional controls, i.e., Cs-modified nanoparticles with control oligo and sugar cargoes, were included to illustrate the negative impact of non-specific interventional stress on tumor growth response. In this combination of mouse and cell line, tumors were observed to be immediately metastatic to lymph nodes and grossly invaded the peritoneal cavity in every mouse but those treated with Formula E (data not shown). Thus, tumor weight is reported as a combination of primary tumor with peritoneal extension and major lymph nodes. Taken together, examples 3 and 4 show the advantageous efficacy of the novel combination of 2R modification and Csnk2a1 and Csnk2a2 sequences across different tumor lines and mouse models.

TABLE 4

Results 14 days after start of treatment in xenograft UM-SCC-47 tumor model

| Treatment | SEQ ID NOS: | Formula from No.[4] | Tumor Burden[5] (g) | % Δ from control | Ki-67 Index (signal area/ nuclear area) | % Δ control | NF-kB Index (signal/tissue area) | % Δ from control |
|---|---|---|---|---|---|---|---|---|
| Experiment E1-Effect of combined 2R modification and oligo mix approach in NIH Athymic nude mouse model |||||||||
| Control | | | 1.27 ± 0.28 | — | 0.58 ± 0.08 | — | 0.71 ± 0.13 | — |
| Control oligo | 2RF7[6] | F | 1.78 ± 0.51 | +40 | 0.66 ± 0.19 | +13.8 | 0.49 ± 0.06 | −31 |
| Sugar cargo | None[7] | | 1.55 ± 0.3 | +22 | 0.67 ± 0.06 | +15.5 | 0.66 ± 0.06 | −7 |
| LCK | 5 | A | 1.38 ± 0.23 | +9 | 0.70 ± 0.07 | +20.7 | 0.54 ± 0.09 | −24 |
| 2RLCK | 5 | B | 1.235 ± 0.09 | −2 | 0.42 ± 0.02 | −27.5 | 0.66 ± 0.04 | −7 |
| 2R huMix | 8 + 9 | E | 0.89 ± 0.25 | −30 | 0.07 ± 0.01* | −89* | 0.18 ± 0.03 | −75* |

Notes:
[1] N = 3 mice per group.
[2] Values are reported as mean ± SE.
[3] * = $p < 0.05$, Student's t test,
[4] Formula number for nanoencapsulated sequence as listed under and described in Example 1.
[5] Tumor burden is reported as cumulative weight of primary tumor with peritoneal extension, brachial, mandibular, and inguinal lymph nodes. Primary and GI tumor were sampled uniformly for microscopy.
[6] Sequence for additional nanoencapsulated control oligo is anti-coagulation Factor VII from Akinc, et al. 2008 Nat Biotechnol 26(5):561-9.
[7] A Cs-modified nanoparticle formulation bearing erythritol was included and prepared similar to Formula A, except that 500 μg of erythritol without any condenser was micellized with 8.75 μg of surfactant, coated with 5.5 mcg of TBG and atomized into a receiving bath modified with 6.25 nM of Mg2+ and 9.38 nM of Sr2+, all other ions the same. Particle diameter were 24 ± 2 nm with a surfact charge of −12 ± 7.8 mev.

Sequences

CK2 alpha (*Homo sapiens* chromosome 20, GRCh38 Primary Assembly; NCBI Reference Sequence: NC_000020.11; 70.52 kb region from base 473322 to 543838; Intl Hu Genome Seq Consort; 2004 *Nature* 431 (7011):931-945)

CK2 alpha prime (*Homo sapiens* chromosome 16, GRCh38 Primary Assembly; NCBI Reference Sequence: NC_000016.10; 39.97 kb region from base 58157907 to 58197878; Martin, et al. 2004 *Nature* 432(7011):988-994)

NM_001896; cDNA sequence for the mRNA sequence of CK2 alpha prime; *Homo sapiens* casein kinase 2, alpha prime polypeptide (CSNK2A2), mRNA (17 Mar. 2008) (SEQ ID NO:11)

NM_177560; cDNA sequence for the mRNA sequence of CK2 alpha; *Homo sapiens* casein kinase 2, alpha 1 polypeptide (CSNK2A1), transcript variant 3, mRNA (12 Mar. 2008) (SEQ ID NO:12)

What is claimed is:

1. A pharmaceutical composition comprising nanoparticles, wherein the nanoparticles comprise: at least one bioactive agent, a surfactant having an hydrophile-lipophile balance (HLB) value of less than 6.0 units, a ligand, and Li$^+$ and Cs$^+$, wherein:
   i) the at least one bioactive agent and the surfactant form a surfactant micelle core;
   ii) the ligand forms a shell which substantially coats the nanoparticles; and
   iii) the nanoparticles have an average diameter of less than about 50 nanometers, and the nanoparticles have increased stability resulting from treatment with Li$^+$ pretreated with Cs$^+$, as compared to nanoparticles treated with (i) Li$^+$ and without Cs$^+$ or (ii) Li$^+$ and Cs$^+$ mixtures but not Li$^+$ pretreated with Cs$^+$ mixtures.

2. The pharmaceutical composition of claim 1, wherein the nanoparticles are prepared using sterile water.

3. The pharmaceutical composition of claim 1, wherein the at least one bioactive agent is a polynucleotide or a plasmid DNA.

4. The pharmaceutical composition of claim 1, wherein:
   i) the at least one bioactive agent comprises a polynucleotide, comprising a 3' RNA portion and a 5' portion comprising DNA, wherein the number 2 position from the 5' end of the polynucleotide is a 2'-OMe modified RNA, wherein a sequence of a portion of the polynucleotide comprises SEQ ID NO: 8 or SEQ ID NO: 9, and
   ii) the ligand is a protein targeting a tenascin receptor.

5. The pharmaceutical composition of claim 4, wherein the protein is tenfibgen.

6. The pharmaceutical composition of claim 1, wherein the Li$^+$ pretreated with Cs$^+$ is in an ion composition.

7. The pharmaceutical composition of claim 1, wherein the ligand comprises a protein, a peptide, a polypeptide, a carbohydrate, polyvinylpyrrolidone (PVP), an antibody, or a biocompatible polymer, or fragments thereof, or a small molecule.

8. The pharmaceutical composition of claim 1, wherein the nanoparticles have enhanced stability, as compared to non-Cs$^+$ treated nanoparticles.

9. A method of administering at least one bioactive agent to a subject, the method comprising administering to the subject the pharmaceutical composition of claim 1.

10. A method for treating a patient with a solid tumor cancer, comprising administering to the patient a therapeutically effective amount of the pharmaceutical composition of claim 1, wherein
   i) the at least one bioactive agent comprises a plurality of polynucleotides, each comprising a 3' RNA portion and a 5' portion comprising DNA, wherein the number 2 position from the 5' end of each polynucleotide is a 2'-OMe modified RNA, wherein the sequence of about 40% to about 60% of the plurality of polynucleotides comprises SEQ ID NO: 8, and the sequence of the remainder of the plurality of polynucleotides comprises SEQ ID NO: 9, and
   ii) the ligand is a protein targeting a tenascin receptor.

11. A method for preparing the pharmaceutical composition of claim 1, the method comprising:
   i) complexing at least one bioactive agent with a condensing agent to form a condensed bioactive agent;
   ii) dispersing the condensed bioactive agent into a water-miscible solvent comprising a surfactant with an hydrophile-lipophile balance (HLB) value of less than 6.0 units to form a surfactant micelle;
   iii) adsorbing a ligand to the exterior surface of the surfactant micelle to form a ligand particle; and
   iv) mixing and incubating the ligand particle with (a) Li+ pre-treated with Cs+ and (b) sterile water to form the composition.

12. The method of claim 8, wherein the at least one bioactive agent is a polynucleotide or plasmid DNA.

13. The method of claim 11, wherein the HLB value of the surfactant is less than about 5 units.

14. A pharmaceutical composition comprising nanoparticles for delivery of a bioactive agent having functional activity to targeted cells in a patient for providing a therapeutic effect on the targeted cells wherein the nanoparticles comprise: at least one bioactive agent, a surfactant having an hydrophile-lipophile balance (HLB) value of less than 6.0 units, and a ligand, wherein:
   i) the at least one bioactive agent is complexed with a condensing agent to form a condensed bioactive agent;
   ii) a surfactant micelle is formed by dispersing the condensed bioactive agent into a water-miscible solvent comprising the surfactant with an HLB value of less than 6.0, and wherein the surfactant micelle has an exterior surface;
   iii) the ligand is substantially adsorbed to the exterior surface of the surfactant micelle to form a ligand particle;
   iv) the ligand particle is mixed and incubated in a stabilization solution comprising (a) Li+ pre-treated with Cs+ and (b) sterile water to form the composition; and
   iv) the nanoparticles have an average diameter of less than about 50 nanometers.

15. The pharmaceutical composition of claim 14, wherein the ligand comprises a protein, a peptide, a polypeptide, a carbohydrate, polyvinylpyrrolidone (PVP), an antibody, or a biocompatible polymer, or fragments thereof, or a small molecule.

16. The pharmaceutical composition of claim 15, wherein the protein is tenfibgen.

17. The pharmaceutical composition of claim 14, wherein the at least one bioactive agent is a polynucleotide that includes a portion of at least 8 consecutive nucleotides of SEQ ID NO: 8.

18. The pharmaceutical composition of claim 14, wherein the at least one bioactive agent is a polynucleotide that includes a portion of at least 8 consecutive nucleotides of SEQ ID NO: 9.

19. The pharmaceutical composition of claim 14, wherein the $Li^+$ ion is derived from Lithium Nitrate.

20. The pharmaceutical composition of claim 14, wherein the nanoparticles are filtered, centrifuged and dried to obtain substantially discrete and non-aggregated nanoparticles.

21. The pharmaceutical composition of claim 14 wherein the stabilization solution comprises about 126 mM $Li^+$ pre-mixed with about 2.5 ppb $Cs^+$.

22. The pharmaceutical composition of claim 14, wherein the HLB value of the surfactant is less than about 5 units.

23. A coated nanoparticle for delivering at least one bioactive agent to an in vitro biological target for assaying the in vitro biological target or an in vivo biological target in a patient for treating the patient, said coated nanoparticle comprising:
   (a) a surfactant-coated complex, wherein the surfactant-coated complex comprises an inner core coated with a surfactant having a hydrophile-lipophile balance (HLB) value of less than about 6 units and the inner core comprises the at least one bioactive agent; and
   (b) a hardened outer shell surrounding the surfactant-coated complex to form the coated nanoparticle, wherein the hardened outer shell comprises a ligand for targeting the biological target when said nanoparticle is administered to the patient; and
   wherein the ligand is adsorbed onto the surfactant-coated complex forming a ligand particle and the ligand particle is stabilized and precipitated with $Li^+$ pretreated with $Cs^+$ in a stabilization bath containing an ion composition comprised of $Li^+$ pretreated with $Cs^+$ to form the coated nanoparticle,
   wherein the coated nanoparticle has a morphological shape selected from the group consisting of spheroid, cuboid and elliptical,
   wherein the coated nanoparticle has a diameter of less than about 50 nanometers, and
   wherein, the coated nanoparticle has enhanced stability.

24. The coated nanoparticle of claim 23, wherein the coated nanoparticle has a molecular weight of greater than 10,000 daltons.

25. The coated nanoparticle of claim 23, wherein the coated nanoparticle has a molecular weight of greater than 20,000 daltons.

26. The coated nanoparticle of claim 23, wherein the coated nanoparticle has a molecular weight of greater than 30,000 daltons.

27. The coated nanoparticle of claim 23, wherein the coated nanoparticle has a diameter of between about 5 and about 50 nanometers.

28. The coated nanoparticle of claim 23, wherein the coated nanoparticle has a diameter of between about 5 and about 40 nanometers.

29. The coated nanoparticle of claim 23, wherein the coated nanoparticle has a diameter of between about 5 and about 30 nanometers.

30. The coated nanoparticle of claim 23, wherein the coated nanoparticle has a diameter of between about 5 and about 20 nanometers.

31. The coated nanoparticle of claim 23, wherein the ion composition includes sterile, water and the $Li^+$ pretreated with $Cs^+$ are present in the ion composition at a ratio of between about 0.1 and about 100 parts $Cs^+$ per billion parts $Li^+$ (ppb).

32. The coated nanoparticle of claim 23, wherein the ion composition includes sterile water, and the $Li^+$ and pretreated with $Cs^+$ are present in the ion composition at a ratio of between about 0.1 and about 5 parts $Cs^+$ per billion parts $Li^+$ (ppb).

33. The coated nanoparticle of claim 23, wherein the ion composition includes sterile water, and the $Li^+$ pretreated with and $Cs^+$ are present in the ion composition at a ratio of between about 0.1 and about 4 parts $Cs^+$ per billion parts $Li^+$ (ppb).

34. The coated nanoparticle of claim 23, wherein the ion composition includes sterile water, and the $Li^+$ pretreated with and $Cs^+$ are present in the ion composition at a ratio of between about 1.2 and about 2.5 parts $Cs^+$ per billion parts $Li^+$ (ppb).

35. The coated nanoparticle of claim 23, wherein the ion composition includes sterile water, and the $Li^+$ pretreated with $Cs^+$ are present in the ion composition at a ratio of between about 2 and about 4 parts $Cs^+$ per billion parts $Li^+$ (ppb).

36. The coated nanoparticle of claim 23, wherein the in vitro or in vivo biological target is biological tissue.

37. The coated nanoparticle of claim 23, wherein the in vitro or in vivo biological target is a biological cell.

38. The coated nanoparticle of claim 23, wherein the in vitro or in vivo biological target is a tumor.

39. The coated nanoparticle of claim 23, wherein the in vitro or in vivo biological target is a molecular target.

40. The coated nanoparticle of claim 23, wherein the hydrophile-lipophile balance (HLB) value is less than about 5 units.

41. The coated nanoparticle of claim 23, wherein the surfactant has a critical micelle concentration of less than about 200 µM.

42. A pharmaceutical composition comprising nanoparticles, wherein the nanoparticles comprise: at least one bioactive agent, a surfactant having an hydrophile-lipophile balance (HLB) value of less than 6.0 units, a ligand, and $Li^+$ and $Cs^+$, wherein:
   i) the at least one bioactive agent and the surfactant form a surfactant micelle core;
   ii) the ligand forms a shell;
   iii) the nanoparticles have an average diameter of less than about 50 nanometers; and
   iv) the nanoparticles are stabilized with an ion composition comprised of $Li^+$ pretreated with $Cs^+$, and the $Cs^+$ and $Li^+$ are present in the ion composition at a ratio of about 0.1 to about 100 parts $Cs^+$ to one billion parts $Li^t$.

43. The pharmaceutical composition of claim 42, wherein the HLB value is less than about 5 units.

44. A pharmaceutical composition comprising nanoparticles, wherein the nanoparticles comprise: at least one bioactive agent, a surfactant having an hydrophile-lipophile balance (HLB) value of less than 6.0 units, a ligand for targeting a biological target, and $Li^+$ and $Cs^+$ derived from $Li^+$ pretreated with $Cs^+$, wherein:
   i) the at least one bioactive agent and the surfactant form a surfactant micelle core;
   ii) the ligand forms a shell around the surfactant micelle core;
   iii) the nanoparticles have an average diameter of less than about 50 nanometers;
   iv) the $Li^+$ pretreated with $Cs^+$ are present in an ion composition ratio of about 0.1 to about 100 parts $Cs^+$ to one billion parts $Li^t$; and
   v) the nanoparticles have enhanced stability, as compared to non-$Cs^+$ treated nanoparticles.

45. The pharmaceutical composition of claim 44, wherein the HLB value is less than about 5 units.

46. A pharmaceutical composition comprising nanoparticles, wherein the nanoparticles comprise: at least one bioactive agent, a surfactant having an hydrophile-lipophile balance (HLB) value of less than 6.0 units, and a ligand for targeting a biological target, wherein:
   i) the at least one bioactive agent and the surfactant form a surfactant micelle core having an exterior surface;
   ii) the ligand is adsorbed to the exterior surface forming a shell around the surfactant micelle core;
   iii) the nanoparticles have an average diameter of less than about 50 nanometers; and
   iv) the nanoparticles have enhanced stability, the enhanced stability resulting from treatment of the nanoparticles with an ion composition comprised of $Li^+$ pretreated with $Cs^+$, wherein the $Cs^+$ and $Li^+$ are present in the ion composition at a ratio of between about 0.1 and about 100 parts $Cs^+$ per billion parts $Li^+$ (ppb).

47. The pharmaceutical composition of claim 46, wherein the HLB value is less than about 5 units.

48. An ion composition for stabilizing nanoparticles, wherein said ion composition comprises $Li^+$ pretreated with $Cs^+$, and nanoparticles comprising a surfactant having an hydrophile-lipophile balance (HLB) value of less than 6.0 units and a ligand.

49. The ion composition of claim 48, wherein the ion composition includes sterile water.

50. The ion composition of claim 48, replaced with "wherein the $Cs^+$ and $Li^+$ are incorporated in the nanoparticles that further comprise at least one bioactive agent, wherein:
   i) the at least one bioactive agent and the surfactant form a surfactant micelle core;
   ii) the ligand forms a shell which substantially coats the nanoparticles;
   iii) the shell incorporates the $Li^+$ and $Cs^+$ ions of the composition of claim 47; and
   iv) the nanoparticles have an average diameter of less than about 50 nanometers;
   wherein said ion composition increases stability of said nanoparticles.

51. The ion composition of claim 48, wherein said ion composition increases stability of nanoparticles, further than (i) nanoparticles treated with $Li^+$ and no $Cs^+$ or (ii) nanoparticles treated with $Li^+$ and $Cs^+$ mixtures and without $Li^+$ pretreated with $Cs^+$.

52. The ion composition of claim 49, wherein the $Cs^+$ and $Li^+$ are incorporated in the nanoparticles that further comprise at least one bioactive agent, wherein:
   i) the at least one bioactive agent and the surfactant form a surfactant micelle core;
   ii) the ligand forms a shell which substantially coats the nanoparticles;
   iii) the shell incorporates the $Li^+$ and $Cs^+$ ions of the composition of claim 47; and
   iv) the nanoparticles have an average diameter of less than about 50 nanometers;
   wherein said ion composition increases stability of said nanoparticles.

53. The ion composition of claim 49, wherein said ion composition increases stability of nanoparticles, further than (i) nanoparticles treated with $Li^+$ and no $Cs^+$ or (ii) nanoparticles treated with $Li^+$ and $Cs^+$ mixtures and without $Li^+$ pretreated with $Cs^+$.

54. The ion of claim 48, wherein the HLB value of the surfactant is less than about 5 units.

55. The ion of claim 52, wherein the HLB value of the surfactant is less than about 5 units.

56. The ion composition of claim 52, wherein nanoparticle has a molecular weight of greater than 10,000 daltons.

57. The ion composition of claim 52, wherein the nanoparticle has a molecular weight of greater than 20,000 daltons.

58. The ion composition of claim 52 wherein the nanoparticle has a molecular weight of greater than 30,000 daltons.

59. The ion composition of claim 52, wherein the nanoparticle has a diameter of between about 5 and about 50 nanometers.

60. The ion composition of claim 52, wherein the nanoparticle has a diameter of between about 5 and about 40 nanometers.

61. The ion composition of claim 52, wherein the nanoparticle has a diameter of between about 5 and about 30 nanometers.

62. The ion composition of claim 52, wherein the nanoparticle has a diameter of between about 5 and about 20 nanometers.

63. The ion composition of claim 52, wherein the $Li^+$ and $Cs^+$ are present in the ion composition at a ratio of between about 0.1 and about 100 parts $Cs^+$ per billion parts $Li^+$ (ppb).

64. The ion composition of claim 52, wherein the $Li^+$ and $Cs^+$ are present in the ion composition at a ratio of between about 0.1 and about 5 parts $Cs^+$ per billion parts $Li^+$ (ppb).

65. The ion composition of claim 52, wherein the $Li^+$ and $Cs^+$ are present in the ion composition at a ratio of between about 0.1 and about 4 parts $Cs^+$ per billion parts $Li^+$ (ppb).

66. The ion composition of claim 52, wherein the $Li^+$ and $Cs^+$ are present in the ion composition at a ratio of between about 1.2 and about 2.5 parts $Cs^+$ per billion parts $Li^+$ (ppb).

67. The ion composition of claim 52, wherein the $Li^+$ and $Cs^+$ are present in the ion composition at a ratio of between about 2 and about 4 parts $Cs^+$ per billion parts $Li^+$ (ppb).

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atgtggagtt tgggttgtat                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgtggagtt tgggctgtat                                                   20

<210> SEQ ID NO 3
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 3
atgtggagct tgggttgtat                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgtggagct tgggctgcat                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
atacaaccca aactccacau                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
atacagccca aactccacau                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
atgcagccca agctccacau                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
auacaaccca aactccacau                                           20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
auacagccca aactccacau                                           20

<210> SEQ ID NO 10
<211> LENGTH: 690
<212> TYPE: DNA
<213> ORGANISM: Homo sapiens

<400> SEQUENCE: 10
atgattggac tcctgtaccc cttccccaag gactgctccc aagcaatgct gaatggagac    60
acgacctctg gcctctacac catttatctg aatggtgata aggctcaggc gctgaagtc    120 ttctgtgaca tgacctctga tggggtgga tggattgtgt cctgagacg caaaaacgga    180 cgcgagaact tctaccaaaa ctggaaggca tatgctgctg gatttgggga ccgcagagaa    240
gaattctggc ttgggctgga caacctgaac aaaatcacag cccaggggca gtacgagctc    300
cgggtggacc tgcgggacca tggggagaca gcctttgctg tctatgacaa gttcagcgtg    360
ggagatgcca agactcgcta caagctgaag gtggagggt acagtgggac agcaggtgac    420
tccatggcct accacaatgg cagatccttc tccacctttg acaaggacac agattcagcc    480
atcaccaact gtgctctgtc ctacaaaggg gctttctggt acaggaactg tcaccgtgtc    540
aacctgatgg ggagatatgg ggacaataac cacagtcagg gcgttaactg gttccactgg    600
aagggccacg aacactcaat ccagtttgct gagatgaagc tgagaccaag caacttcaga    660
aatcttgaag gcaggcgtaa gcgggcataa                                    690

<210> SEQ ID NO 11
<211> LENGTH: 1674
<212> TYPE: DNA
<213> ORGANISM: Homo sapiens

<400> SEQUENCE: 11
gcggccgccc gccgccgcgc tcctcctcct cctcctccag cgcccggcgg cccgctgcct    60
cctccgcccg acgccccgcg tccccgcccg cgccgccgcc gccaccctct gcgccccgcg    120 ccgcccccg gtcccgcccg ccatgccgg cccggccgcg ggcagcaggg cccgggtcta    180
cgccgaggtg aacagtctga ggagccgcga gtactgggac tacgaggctc acgtcccgag    240
ctggggtaat caagatgatt accaactggt tcgaaaactt ggtcggggaa aatatagtga    300
agtatttgag gccattaata tcaccaacaa tgagagagtg ttgtaaaaa tcctgaagcc    360 agtgaagaaa aagaagataa acgagaggt taagattctg gagaaccttc gtggtggaac    420
aaatatcatt aagctgattg acactgtaaa ggacccgtg tcaaagacac cagctttggt    480
atttgaatat atcaataata cagattttaa gcaactctac cagatcctga cagactttga    540

-continued

```
tatccggttt tatatgtatg aactacttaa agctctggat tactgccaca gcaagggaat      600
catgcacagg gatgtgaaac ctcacaatgt catgatagat caccaacaga aaaagctgcg      660
actgatagat tggggtctgg cagaattcta tcatcctgct caggagtaca atgttcgtgt      720
agcctcaagg tacttcaagg gaccagagct cctcgtggac tatcagatgt atgattatag      780
cttggacatg tggagtttgg gctgtatgtt agcaagcatg atctttcgaa gggaaccatt      840
cttccatgga caggacaact atgaccagct tgttcgcatt gccaaggttc tgggtacaga      900
agaactgtat gggtatctga agaagtatca catagaccta gatccacact tcaacgatat      960
cctgggacaa cattcacgga aacgctggga aaactttatc catagtgaga acagacacct     1020
tgtcagccct gaggccctag atcttctgga caaacttctg cgatacgacc atcaacagag     1080
actgactgcc aaagaggcca tggagcaccc atacttctac cctgtggtga aggagcagtc     1140
ccagccttgt gcagacaatg ctgtgctttc cagtggtctc acggcagcac gatgaagact     1200
ggaaagcgac gggtctgttg cggttctccc acttttccat aagcagaaca gaaccaaat      1260
caaacgtctt aacgcgtata gagagatcac gttccgtgag cagacacaaa acggtggcag     1320
gtttggcgag cacgaactag accaagcgaa gggcagccca ccaccgtata tcaaacctca     1380
cttccgaatg taaaaggctc acttgccttt ggcttcctgt tgacttcttc ccgacccaga     1440
aagcatgggg aatgtgaagg gtatgcagaa tgttgttggt tactgttgct ccccgagccc     1500
ctcaactcgt cccgtggccg cctgtttttc cagcaaacca cgctaactag ctgaccacag     1560
actccacagt gggggacgg gcgcagtatg tggcatggcg gcagttacat attattattt       1620
taaaagtata tattattgaa taaaaggttt taaaagaaaa aaaaaaaaa aaaa             1674
```

<210> SEQ ID NO 12
<211> LENGTH: 2522
<212> TYPE: DNA
<213> ORGANISM: Homo sapiens

<400> SEQUENCE: 12

```
cccgcctcct ggtaggaggg ggtttccgct tccggcagca gcggctgcag cctcgctctg       60
gtccctgcgg ctggcggccg agccgtgtgt ctcctcctcc atcgccgcca tattgtctgt      120
gtgagcagag gggagagcgg ccgccgccgc tgccgcttcc accacagaaa tcaagatgac      180
taccagctgt ttcgaaaatt aggccgaggt aaatacagtg aagtatttga agccatcaac      240
atcacaaata atgaaaaagt tgttgttaaa attctcaagc cagtaaaaaa gaagaaaatt      300
aagcgtgaaa taaagatttt ggagaatttg agaggaggtc ccaacatcat cacactggca      360
gacattgtaa aagaccctgt gtcacgaacc cccgccttgg ttttttgaaca cgtaaacaac      420
acagacttca gcaattgta ccagacgtta acagactatg atattcgatt ttacatgtat       480
gagattctga aggccctgga ttattgtcac agcatgggaa ttatgcacag atgtcaag       540
ccccataatg tcatgattga tcatgagcac agaaagctac gactaataga ctggggtttg      600
gctgagtttt atcatcctgg ccaagaatat aatgtccgag ttgcttcccg atacttcaaa      660
ggtcctgagc tacttgtaga ctatcagatg tacgattata gtttggatat gtggagtttg      720
ggttgtatgc tggcaagtat gatctttcgg aaggagccat ttccatgg acatgacaat       780
tatgatcagt tggtgaggat agccaaggtt ctggggacag aagatttata tgactatatt      840
gacaaataca acattgaatt agatccacgt tcaatgata tcttgggcag acactctcga       900
aagcgatggg aacgctttgt ccacagtgaa atcagcacc ttgtcagccc tgaggccttg       960
gatttcctgg acaaactgct gcgatatgac caccagtcac ggcttactgc aagagaggca     1020
```

-continued

```
atggagcacc cctatttcta cactgttgtg aaggaccagg ctcgaatggg ttcatctagc    1080
atgccagggg gcagtacgcc cgtcagcagc gccaatatga tgtcagggat ttcttcagtg    1140 ccaaccoctt cacccottgg acctctggca ggctcaccag tgattgctgc tgccaacccc    1200
cttgggatgc ctgttccagc tgccgctggc gctcagcagt aacggcccta tctgtctcct    1260
gatgcctgag cagaggtggg ggagtccacc ctctccttga tgcagcttgc gcctggcggg    1320
gaggggtgaa acacttcaga agcaccgtgt ctgaaccgtt gcttgtggat ttatagtagt    1380
tcagtcataa aaaaaaaatt ataataggct gattttcttt tttcttttt tttttaactc    1440 gaactttca taactcaggg gattccctga aaaattacct gcaggtggaa tatttcatgg    1500 acaaatttt ttttctcccc tcccaaattt agttcctcat cacaaaagaa caaagataaa    1560
ccagcctcaa tcccggctgc tgcatttagg tggagacttc ttcccattcc caccattgtt    1620
cctccaccgt cccacacttt aggggtttgg tatctcgtgc tcttctccag agattacaaa    1680
aatgtagctt ctcaggggag gcaggaagaa aggaaggaag gaaagaagga agggaggacc    1740
caatctatag gagcagtgga ctgcttgctg gtcgcttaca tcactttact ccataagcgc    1800
ttcagtgggg ttatcctagt ggctcttgtg gaagtgtgtc ttagttacat caagatgttg    1860
aaaatctacc caaaatgcag acagatacta aaaacttctg ttcagtaaga atcatgtctt    1920
actgatctaa ccctaaatcc aactcattta tactttatt tttagttcag tttaaaatgt    1980
tgataccttc cctcccaggc tccttacctt ggtcttttcc ctgttcatct cccaacatgc    2040
tgtgctccat agctggtagg agagggaagg caaaatcttt cttagttttc tttgtcttgg    2100
ccattttgaa ttcatttagt tactgggcat aacttactgc tttttacaaa agaaacaaac    2160
attgtctgta caggtttcat gctagagcta atgggagatg tggccacact gacttccatt    2220
ttaagctttc taccttcttt tcctccgacc gtccccttcc ctcacatgcc atccagtgag    2280
aagacctgct cctcagtctt gtaaatgtat cttgagaggt aggagcagag ccactatctc    2340
cattgaagct gaaatggtag acctgtaatt gtgggaaaac tataaactct cttgttacag    2400
ccccgccacc ccttgctgtg tgtatatata taatactttg tccttcatat gtgaaagatc    2460
cagtgttgga attctttggt gtaaataaac gtttggtttt atttatcaaa aaaaaaaaaa    2520
aa                                                                  2522
```